(12) United States Patent
Wolf, II

(10) Patent No.: US 8,239,038 B2
(45) Date of Patent: Aug. 7, 2012

(54) APPARATUS AND METHOD USING NEAR INFRARED REFLECTOMETRY TO REDUCE THE EFFECT OF POSITIONAL CHANGES DURING SPINAL CORD STIMULATION

(76) Inventor: Erich W. Wolf, II, Lake Charles, LA (US)

( * ) Notice: Subject to any disclaimer, the term of this patent is extended or adjusted under 35 U.S.C. 154(b) by 44 days.

(21) Appl. No.: 12/925,231

(22) Filed: Oct. 14, 2010

(65) Prior Publication Data

US 2012/0095525 A1    Apr. 19, 2012

(51) Int. Cl.
*A61N 1/08* (2006.01)

(52) U.S. Cl. ............ 607/62; 607/117; 607/46; 600/424; 600/473

(58) Field of Classification Search .............. 607/62, 607/117; 600/424, 473
See application file for complete search history.

(56) References Cited

U.S. PATENT DOCUMENTS

| | | | |
|---|---|---|---|
| 5,824,021 A | 10/1998 | Rise | |
| 6,058,331 A | 5/2000 | King | |
| 6,120,467 A | 9/2000 | Schallhorn | |
| 6,169,924 B1 | 1/2001 | Meloy et al. | |
| 6,587,724 B2 | 7/2003 | Mann | |
| 6,622,048 B1 | 9/2003 | Mann et al. | |
| 6,871,099 B1 | 3/2005 | Whitehurst et al. | |
| 7,127,296 B2 | 10/2006 | Bradley | |
| 7,162,304 B1 | 1/2007 | Bradley | |
| 7,216,000 B2 | 5/2007 | Sieracki et al. | |
| 7,263,402 B2 | 8/2007 | Thacker | |
| 7,330,762 B2 | 2/2008 | Boveja | |
| 7,333,857 B2 | 2/2008 | Campbell | |
| 7,359,751 B1 | 4/2008 | Erickson et al. | |
| 7,463,927 B1 | 12/2008 | Chaouat | |
| 7,539,543 B2 | 5/2009 | Schiff et al. | |
| 7,650,190 B2 | 1/2010 | Zhou et al. | |

(Continued)

FOREIGN PATENT DOCUMENTS

WO    WO2007059362 A2    5/2007

OTHER PUBLICATIONS

Scott Prahl, Tabulated Molar Extinction Coefficient for Hemoglobin in Water, http://omlc.ogi.edu/spectra/hemoglobin/summary.html, Mar. 4, 1998, pp. 1-7.

(Continued)

*Primary Examiner* — Carl H Layno
*Assistant Examiner* — Yun Haeng H Lee
(74) *Attorney, Agent, or Firm* — Schultz & Associates, P.C.

(57) ABSTRACT

A spinal cord stimulation apparatus and method for automatic adjustments of SCS using near-infrared (NIR) reflectometry are provided. A positionally sensitive system for spinal cord stimulation including an electrode assembly with integrated optical components for sensing spinal cord position relative to a stimulating electrode array and an SCS controller for controlling electrode stimulation parameters is provided. The integrated optical components include an IR emitter and a pair of IR photodetectors. As light from the IR emitter reflects from the spinal cord, it is detected by each of the pair of IR photodetectors. As the spinal cord changes position so do the angles of incidence for detected light from the IR emitter, a ratio of optical intensities in combination with a total optical intensity is measured and used to interpolate a set of electrode stimulation settings from a calibration table. Electrode pulse characteristics are adjusted in real time to minimize changes in stimulation perceived by the patient during motion.

39 Claims, 17 Drawing Sheets

U.S. PATENT DOCUMENTS

| | | |
|---|---|---|
| 7,684,869 B2 * | 3/2010 | Bradley et al. .......... 607/62 |
| 2007/0027514 A1 | 2/2007 | Gerber |
| 2009/0118787 A1 | 5/2009 | Moffitt et al. |
| 2009/0270960 A1 | 10/2009 | Zhao et al. |
| 2010/0105997 A1 * | 4/2010 | Ecker et al. .......... 600/334 |

OTHER PUBLICATIONS

URS Utzinger, Oxygen saturation, http://www2.engr.arizona.edu/~bme517/supporting%20documents/PulseOximeter/Pulse%20Oxi%20Meter%20Laboratory.htm#_Toc67647950, 2002, pp. 1-24.

* cited by examiner

FRONT, 0°

RIGHT, 90°

BACK, 180°

LEFT, 270°

| PATIENT POSITION | PHOTO-DETECTOR $PD_L$ | PHOTO-DETECTOR $PD_R$ | LEFT PULSE AMPLITUDE | RIGHT PULSE AMPLITUDE | PULSE WIDTH | PULSE FREQUENCY |
|---|---|---|---|---|---|---|
| 1 (FRONT) 0° | $PD_{L1}$ | $PD_{R1}$ | $A_{L1}$ | $A_{R1}$ | $P_{W1}$ | $P_{f1}$ |
| 2 (RIGHT) 90° | $PD_{L2}$ | $PD_{R2}$ | $A_{L2}$ | $A_{R2}$ | $P_{W2}$ | $P_{f2}$ |
| 3 (BACK) 180° | $PD_{L3}$ | $PD_{R3}$ | $A_{L3}$ | $A_{R3}$ | $P_{W3}$ | $P_{f3}$ |
| 4 (LEFT) 270° | $PD_{L4}$ | $PD_{R4}$ | $A_{L4}$ | $A_{R4}$ | $P_{W4}$ | $P_{f4}$ |

APPARATUS AND METHOD USING NEAR INFRARED REFLECTOMETRY TO REDUCE THE EFFECT OF POSITIONAL CHANGES DURING SPINAL CORD STIMULATION

FIELD OF INVENTION

This invention relates generally to spinal cord stimulation (SCS) and technique for automatic adjustments of SCS using near-infrared (NIR) reflectometry.

BACKGROUND

Spinal cord stimulation is a technique which uses an implanted electrode array to control chronic pain. The electrode array is typically implanted in a fixed position within the epidural space near the spinal cord. A signal generator delivers current pulses to the spinal cord via the implanted electrode array. The current pulses induce parasthesiae which help block the perception of pain.

In FIG. 1, spinal column 1 is shown to have a number of vertebrae, categorized into four sections or types: lumbar vertebrae 2, thoracic vertebrae 3, cervical vertebrae 4 and sacral vertebrae 5. Cervical vertebrae 4 include the 1st cervical vertebra (C1) through the 7th cervical vertebra (C7). Just below the 7th cervical vertebra is the first of twelve thoracic vertebrae 3 including the 1st thoracic vertebra (T1) through the 12th thoracic vertebra (T12). Just below the 12th thoracic vertebrae 3, are five lumbar vertebrae 2 including the 1st lumbar vertebra (L1) through the 5th lumbar vertebra (L5), the 5th lumbar vertebra being attached to sacral vertebrae 5 (S1 to S5), sacral vertebrae 5 being naturally fused together in the adult.

In FIG. 2, representative thoracic vertebra 10 is shown to have a number of notable features which are in general shared with lumbar vertebrae 2 and cervical vertebrae 4. The thick oval segment of bone forming the anterior aspect of vertebra 10 is vertebral body 12. Vertebral body 12 is attached to bony vertebral arch 13 through which spinal nerves 19 run. Vertebral arch 13, forming the posterior of vertebra 10, is comprised of two pedicles 14, which are short stout processes that extend from the sides of vertebral body 12 and bilateral laminae 15. The broad flat plates that project from pedicles 14 and join in a triangle to form a hollow archway, spinal canal 16. Spinous process 17 protrudes from the junction of bilateral laminae 15. Transverse processes 18 project from the junction of pedicles 14 and bilateral laminae 15. The structures of the vertebral arch protect spinal cord 20 and spinal nerves 19 that run through the spinal canal.

Surrounding spinal cord 20 is dura 21 that contains cerebrospinal fluid (CSF) 22. Epidural space 24 is the outermost part of the spinal canal. It is the space within the spinal canal formed by the surrounding vertebrae lying outside the dura.

Referring to FIGS. 1, 2 and 3, the placement of an electrode array for spinal cord stimulation according to the prior art is shown. Electrode array 30 is positioned in epidural space 24 between dura 21 and the walls of spinal canal 16 towards the dorsal aspect of the spinal canal nearest bilateral laminae 15 and spinous process 17.

FIG. 4 shows a prior art electrode array 30 including a set of electrode contacts 35 sealed into elastomeric housing 36. Electrode array 30 has a set of electrode leads 31 which are connected to electrical pulse generator 32. The electrical pulse generator may be outside of the body or it may be implanted subcutaneously. Each electrode contact has a separate electrical conductor in the set of electrode leads 31 so that the current to each contact may be independently conducted and controlled.

The anatomical distribution of parasthesiae is dependent upon the spatial relationship between a stimulating electric field generated by the electrode array and the neuronal pathways within the spinal cord. The distribution may be changed by altering the current across one or more electrodes of the electrode array. Changing anode and cathode configurations of the electrode array also alters the distribution and hence, the anatomical pattern of the induced parasthesiae.

Proper intensity of the current pulses is important. Excessive current produces an uncomfortable sensation. Insufficient current produces inadequate pain relief. Body motion, particularly bending and twisting, causes undesired and uncomfortable changes in stimulation due to motion of the spinal cord relative to the implanted electrode array.

There are methods and systems for controlling implanted devices within the human body. For example, Ecker et al, in U.S. Patent Application No. 2010/0105997, discloses an implantable medical device that includes a controller and a plurality of sensor modules. A sensor includes at least one light source that emits light at a particular wavelength, which scatters through blood-perfused tissue a detector senses the light reflected by blood mass of a patient.

U.S. Pat. No. 7,684,869 to Bradley, et al. discloses a system using an interelectrode impedance to determine the relative orientation of a lead other leads in the spinal column. Bradley et al. further disclose that interelectrode impedance may be used to adjust stimulation energy.

U.S. Patent Application No. 2009/0118787 to Moffitt, et al. discloses electrical energy conveyed between electrodes to create a stimulation region. Physiological information from the patient is acquired and analyzed to locate a locus of the stimulation region. The stimulation region is electronically displaced.

Deficiencies exist in the prior art related to accuracy of spinal cord stimulation in relieving pain under changing circumstances. The deficiencies are most pronounced while the patient is moving. The prior art does not provide a satisfactory way to automatically adjust spinal cord stimulation to compensate for motion between the electrodes and the spinal cord to maintain a constant level of pain relief during patient motion.

SUMMARY OF PREFERRED EMBODIMENTS

Embodiments of the present invention operate to automatically adjust spinal cord stimulation to compensate for patient movement. Automatic adjustment results in consistent parasthesiae and conservation of battery power.

A preferred embodiment includes an electrode array incorporating a centrally positioned infrared (IR) emitter bracketed by a set of electrodes. Adjacent the electrodes are a pair of photodetectors. The IR emitter and photodetectors are positioned facing the spinal cord. Light emitted from the IR emitter is reflected from the spinal cord and detected by the photodetectors. The first photodetector detects light at a first angle as measured from an optical axis of the IR emitter and generates a first current signal. The second photodetector detects light at a second angle as measured from the optical axis of the IR emitter and generates a second current signal. The detected current signals are used to vary the stimulation current delivered to the electrodes based on a calibration table. The varying current adjusts the induced electric field of each electrode to compensate for changes in the position of the spinal cord to achieve a constant electric field.

A method for calibration is also provided that creates the calibration table. The calibration table is used to store optimal current settings for the electrodes for several known physiological positions of the patient.

In another embodiment, provisions are made for remotely controlled operation of the stimulator. In this embodiment, a communications link is established between a remote calibration computer and the spinal cord stimulator to upload and download data.

BRIEF DESCRIPTION OF DRAWINGS

The following disclosure is understood best in association with the accompanying figures. Like components share like numbers.

DETAILED DESCRIPTION

Figure 1:
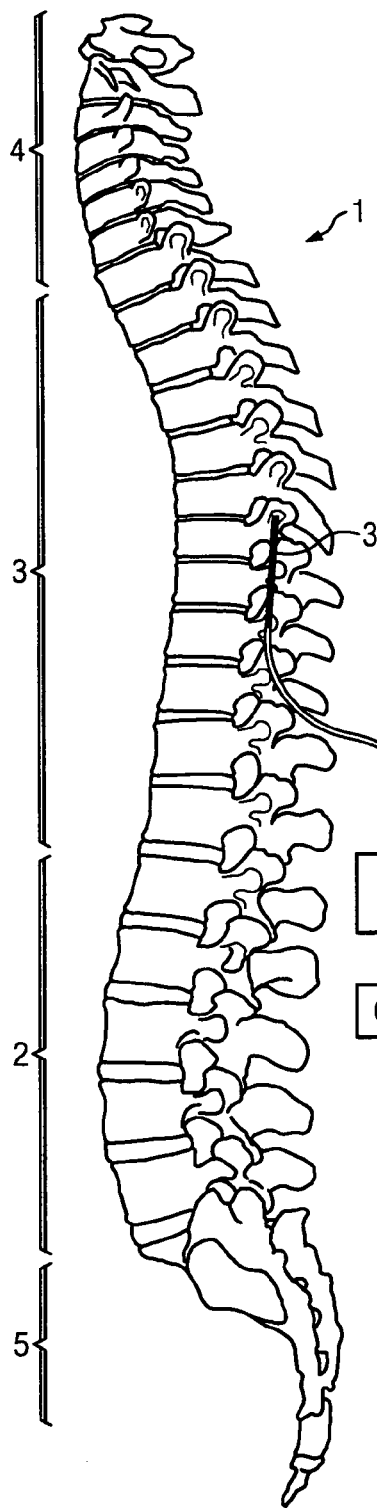
FIG. 1 shows a view of the human spine showing the various types of vertebrae and an approximate position of an electrode array for spinal cord stimulation.
Figure 4:
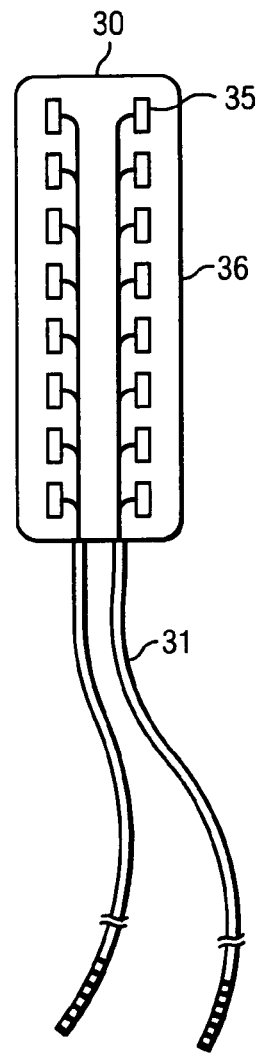
FIG. 4 shows a prior art electrode array for spinal cord stimulation.
Figure 2:
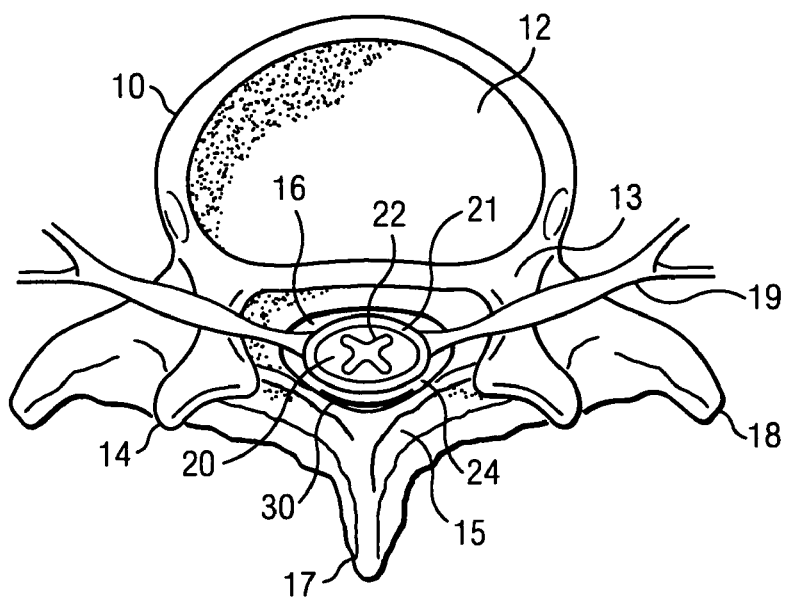
FIG. 2 shows a transverse view of a thoracic vertebra indicating the position of the spinal cord and an electrode array for spinal cord stimulation.
Figure 3:
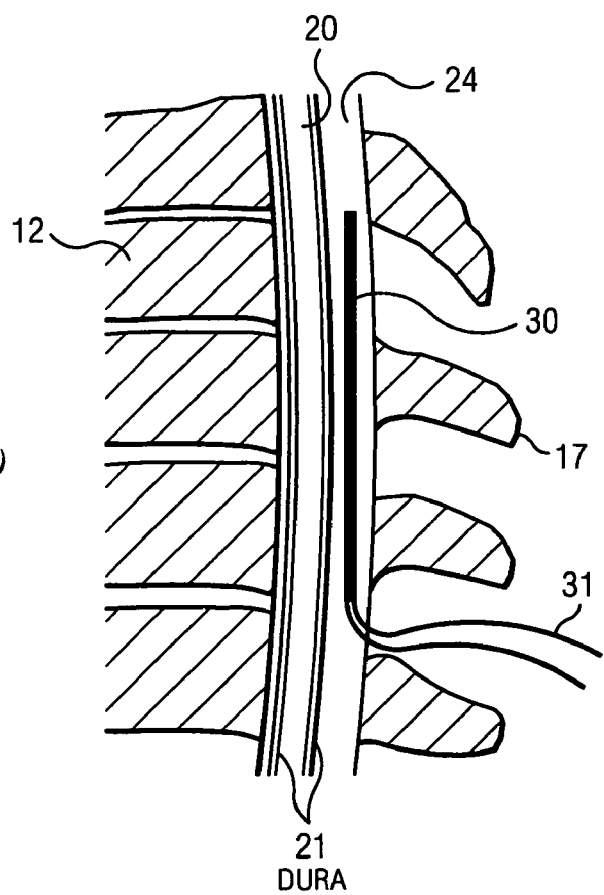
FIG. 3 shows a sagital cross section view of the human spine showing the approximate position of an electrode array for spinal cord stimulation.

The distance between a stimulating electrode and the spinal cord surface may be inferred from a function dependent upon: 1) the optical path lengths of light between an IR emitter and a set of photodetectors, where the light is reflected from the spinal cord; 2) the spinal cord geometry; 3) the optical divergence of the IR emitter; and 4) the presence of chromophores in the optical path.

The dura surrounding the spinal cord itself is translucent to near infrared light. Near infrared light will be scattered by, and will reflect from the spinal cord. Cerebrospinal fluid will negligibly scatter near infrared light, but will not act as a significant reflector of near-infrared light. Light from the emitter passes through thin, relatively avascular, dura, to enter cerebrospinal fluid, CSF, which produces very little scattered light. Light incident on spinal cord experiences scatter resulting in a portion being reflected and another portion being absorbed by chromophores.

Optical absorption in fluid medium may be described by the Beer-Lambert Law (Beer's Law), which is reasonably accurate for a range of chromophores and concentrations. Beer's Law, states that the optical absorbance of a fluid with a chromophore concentration varies linearly with path length through the fluid and the chromophore concentration as:

$$A_\lambda = \epsilon_\lambda bc, \qquad (1)$$

where:
$\epsilon_\lambda$=molar absorptivity or extinction coefficient of the chromophore at wavelength $\lambda$ (the optical density of a 1-cm thick sample of a 1 M solution);
b=sample path length in centimeters; and
c=concentration of the compound in the sample, in molarity (mol L−1).

The absorbance ($A_\lambda$) at a wavelength $\lambda$ is related to the ratio of light energy passing through the fluid, I, to the incident light energy, $I_0$, in $$A_\lambda = -\log(I/I_0). \qquad (2)$$

For deoxyhemoglobin and oxyhemoglobin, the extinction coefficient spectra are well known.

The path length within the spinal cord is dependent upon the geometry of the ellipsoid shaped spinal cord and its normal vector relative to the optical axes of the emitter and detector pair.

The optical path length within CSF is roughly equal to the nominal geometric path length as the scatter is small and the index of refraction does not vary considerably along the path. Light absorption of the CSF may be approximated by that of its primary constituent, $H_2O$. Sensitivity of the system to CSF path length may be optimized using a light wavelength at a local maxima of the water extinction coefficient curve near 950-1000 nm.

When considering the emitter wavelength, one must also consider the extinction coefficients of the primary chromophores, deoxy- and oxy-hemoglobin. To minimize effects of blood flow changes within the spinal cord (although these are thought to be insignificant in the quasi-static sense), one may select the isosbestic wavelength of these chromophore species, preferably at about 805 nm.

The geometry of the emitter-detector pair relative to the spinal cord is the parameter most prone to variability. The variance results from factors such as dependence upon placement of the electrode within the spinal canal, canal diameter, spinal cord shape, spinal cord caliber, and presence of scoliotic or kyphotic curvature within the spine. Consequently, this geometric parameter is the primary reason that the system must be calibrated, in situ, in vivo. Spinal cord position may then be inferred through various methods from data obtained at extremes of body position.

The effects of geometry may be minimized by minimizing the angle between the emitter and detector optical axes relative to the spinal cord surface normal vector.

The beam divergence of the emitter relative to the incident and reflected rays will influence the detected light amplitude.

It is desirable to maintain a constant electric field at a group of target cells in the spinal cord as the spinal cord moves in order to consistently reduce the transmission of a pain sensation to the brain. As the patient bends forward to 0°, the spinal cord moves forward in its orbit in the spinal canal. An equal increase in stimulation pulse amplitude for each electrode pair is required to maintain the same electric field density. As the patient bends to the right 90°, the spinal cord moves to the right in its orbit in the spinal canal. A decrease in electrode stimulation pulse amplitude in the right electrode and an increase in electrode stimulation pulse amplitude in the left electrode of the electrode pair is required. As the patient bends backward to 180°, the spinal cord moves back in its orbit in the spinal canal. A decrease in electrode stimulation pulse amplitude is required to maintain a constant electric field across the spinal cord. As the patient bends to the left to 270°, the spinal cord moves to the left in its orbit. A decrease in electrode stimulation pulse amplitude in the left electrode and an increase in electrode stimulation pulse amplitude in the right electrode of the electrode pair is required.

Figure 5A:
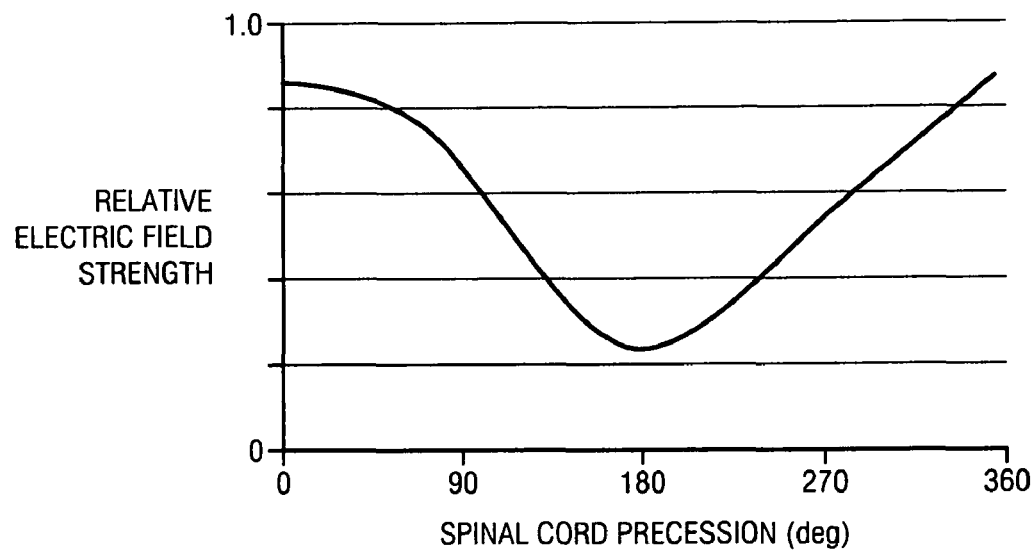
FIGS. 5a and 5b show the relative electric field produced by a preferred embodiment as a spinal cord precesses about an orbit in the spinal canal.
Figure 5B:
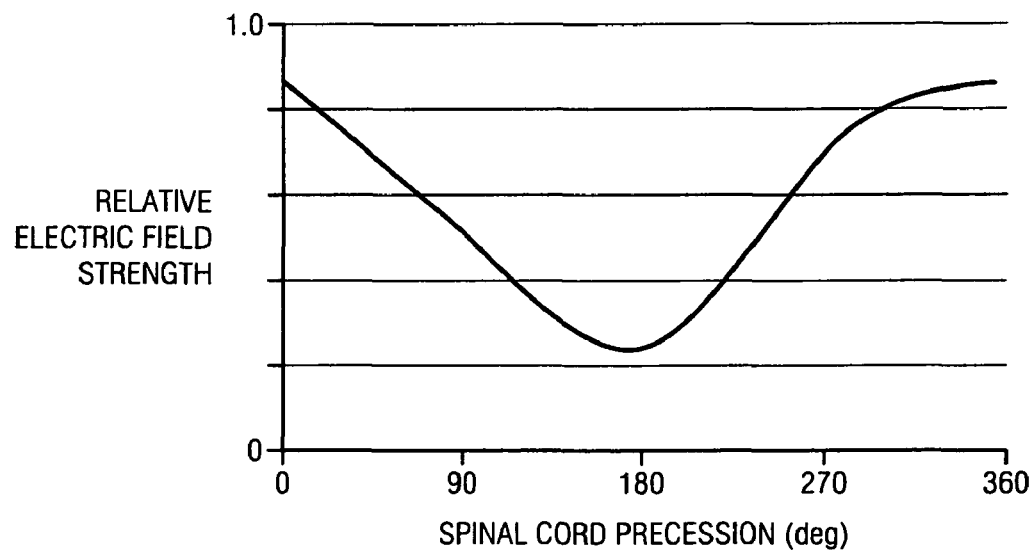

FIGS. 5a and 5b show the relative electric field intensity required to be generated at a left and right electrode, respectively, for maintenance of a constant field at any point across in a horizontal cross section of the spinal cord as the spinal cord is moved through an orbit of 360° in the spinal canal.

Referring to FIGS. 6a through 6d, the positional relationship between the IR emitters, the photodetectors and the electrodes during spinal movement will be described.

Figure 6A:
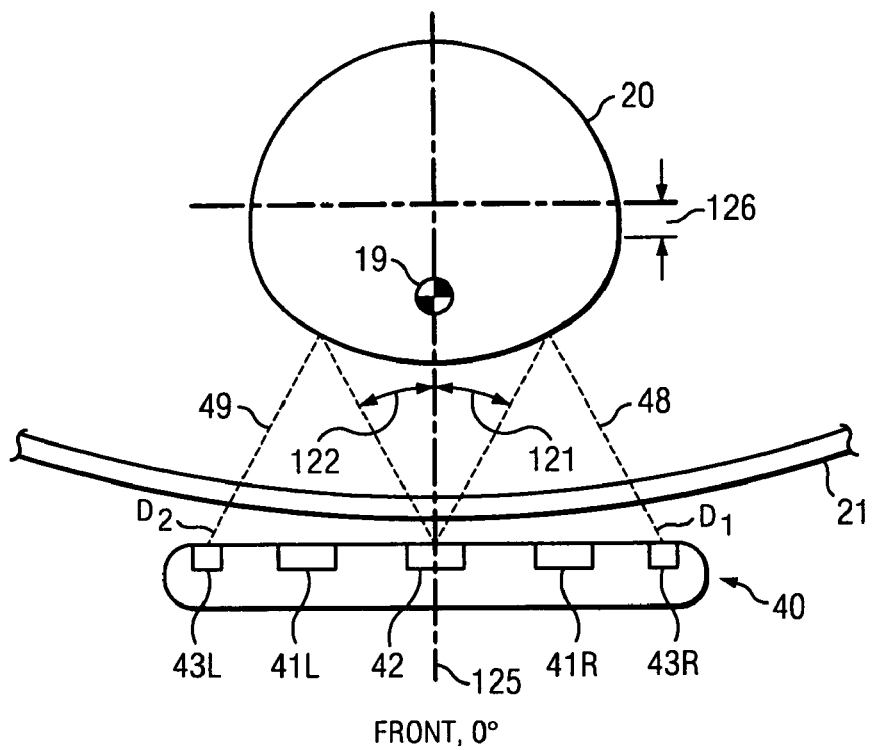
FIG. 6a shows a cross-sectional view of an electrode array centrally located in relation to a spinal cord at 0° displacement.

Referring to FIG. 6a, spinal cord 20 is positioned forward at a 0° location in the spinal canal. Electrode array 40 is implanted outside dura 21. IR emitter 42 is centrally positioned on optical axis 125. Electrodes 41L and 41R are positioned toward the dura and within an operational range of target cells 19. Photodetectors 43L and 43R are positioned within an operational range of spinal cord 20. Target cells 19 are positioned within spinal cord 20 in an arbitrary but constant position with respect to the spinal cord.

In operation, IR emitter 42 produces light ray 48 which forms an angle 121 with optical axis 125. Light ray 48 is reflected from spinal cord 20 and enters photodetector 43R thereby producing an electrical current. IR emitter 42 also produces light ray 49 which forms angle 122 with optical axis 125. Light ray 49 is reflected from spinal cord 20 and enters photodetector 43L thereby producing an electric current. An electric field produced by electrode 41R is produced reaching target cells 19. Similarly, an electric field produced by electrode 41L is produced reaching target cells 19. Amplitudes $A_L$ and $A_R$ are the current to drive both the left and the right electrode, respectively. Both are relatively high. Light ray 48 traverses a distance $D_1$ between IR emitter 42 and photodetector 43R. Light ray 49 traverses a distance of $D_2$ between IR emitter 42 and electrode 41L. The distances $D_1$ and $D_2$ are roughly equal and both relatively high. The photocurrents produced by the photodetectors are roughly equal.

Figure 6B:
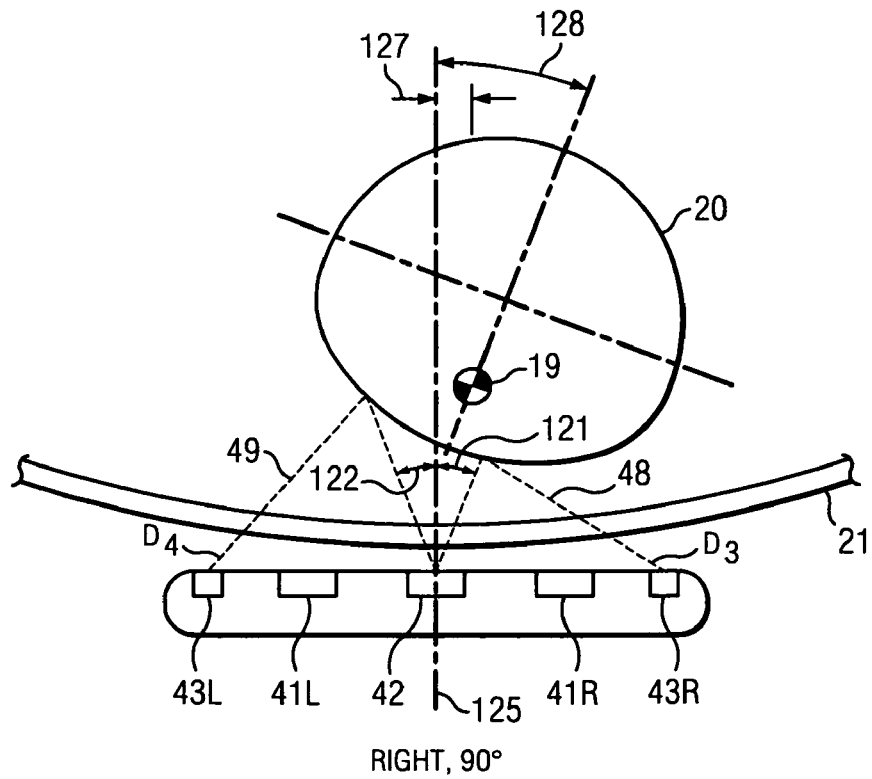
FIG. 6b shows a cross-sectional view of an electrode array centrally located in relation to a spinal cord at 90° displacement.

Referring to FIG. 6b, the spinal cord is shifted to the right 90° position by rotation through angle 128 and linear translation 127.

In operation, IR emitter 42 produces light ray 48 which forms an angle 121 with optical axis 125. Light ray 48 is reflected from spinal cord 20 and is received by photodetector 43R. IR emitter 42 also produces light ray 49 which forms an angle 122 with optical axis 125. Light ray 48 is reflected from spinal cord 20 and is received by photodetector 43R. Light ray 49 is reflected from spinal cord 20 and is received by photodetector 43L. The distance from electrode 41L, to the target cells is relatively high compared to the distance from electrode 41R. Hence, the current amplitude for electrode 43L is relatively high compared to that of the electrode 43R. The total distance traversed for light ray 48 is distance $D_3$. The total distance traversed by light ray 49 is distance $D_4$. It can be seen that distance $D_3$ is lesser than distance $D_1$ and distance $D_2$ and is relatively low. Distance $D_4$ is approximately equal to distance $D_1$ and distance $D_2$. The photocurrent produced by photodetector 43L is relatively low compared to the photocurrent produced by photodetector 43R.

Figure 6C:
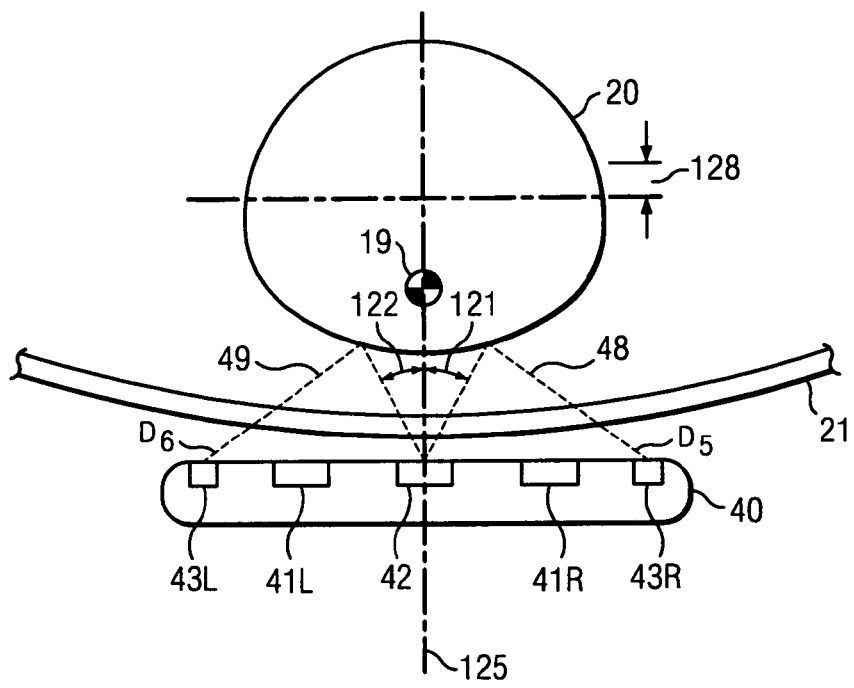
FIG. 6c shows a cross-sectional view of an electrode array centrally located in relation to a spinal cord at 180° displacement.
Figure 6D:
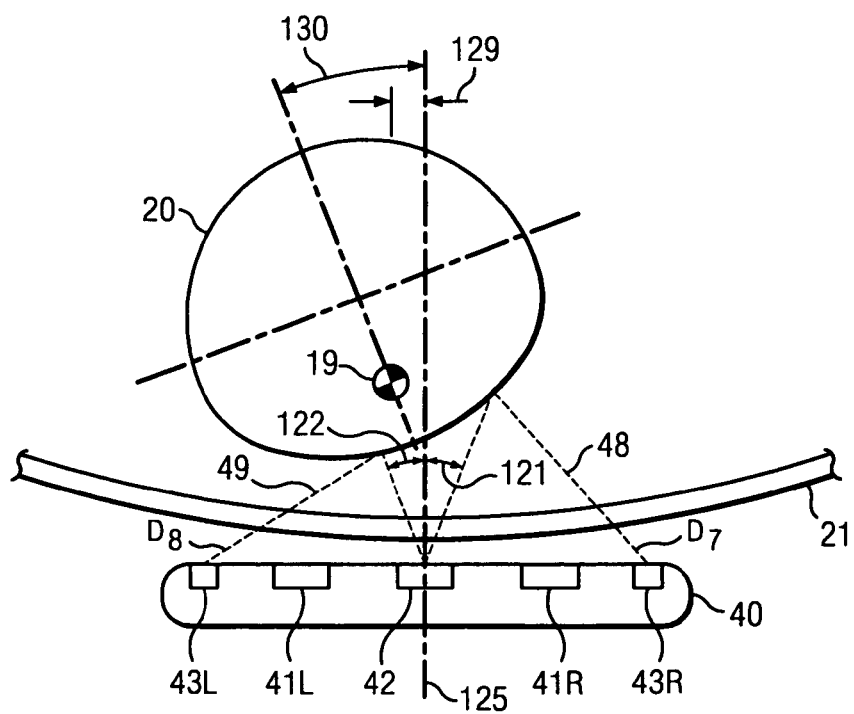
FIG. 6d shows a cross-sectional view of an electrode array centrally located in relation to a spinal cord at 270° displacement.

Referring to FIG. 6c, spinal cord 20 is positioned rearward at a 180° location in the spinal canal with a linear translation 126 with respect to the 0° location.

In operation, IR emitter 42 produces light ray 48 which forms an angle 121 with optical axis 125. Light ray 48 is reflected from spinal cord 20 and enters photodetector 43R. IR emitter 42 also produces light ray 49 which forms an angle 122 with optical axis 125. Light ray 49 is reflected from spinal cord 20 and is received by photodetector 43L. The distances from left electrode 41L and right electrode 41R to the target cells are both relatively low. Hence, the amplitudes of the current to the electrodes $A_L$ and $A_R$ are relatively low compared to FIGS. 6a and 6b. Light ray 48 traverses the distance $D_5$ between IR emitter 42 and photodetector 43R. Light ray 49 traverses a distance $D_6$ between IR emitter 42 and photodetector 43L. It can be seen that distances $D_5$ and $D_6$ are approximately equal. Further, distances $D_5$ and $D_6$ are less than distances $D_1$ and $D_2$. The photocurrents produced by both photodetectors are relatively high compared to the photocurrents of FIG. 6a.

Referring to 6d, the spinal cord is shifted in position by rotation through angle 130 and linear translation 129. The 270° shifted position corresponds to a bend of the patient to left.

In operation, IR emitter 42 produces light ray 49 which forms an angle 122 with optical axis 125. IR emitter 42 also produces light ray 48 which forms angle 121 with optical axis 125. Light ray 49 is reflected from spinal cord 20 and is received by photodetector 43L. Light ray 48 is reflected from spinal cord 20 and is received by photodetector 43R. The distance from left electrode 41L to the target cells is relatively low compared to the distance from the right electrode 41R to the target cells. Hence, the current amplitude for electrode 41L is relatively low compared to the current for right electrode 43R. The distance traversed for light ray 49 is distance $D_8$. The distance traversed for light ray 48 is $D_7$. It can be seen that distance $D_7$ is greater than distance $D_8$. It can also be seen that distance $D_7$ is approximately equal to distances $D_1$ and $D_2$. It can further be seen that distance $D_8$ is approximately equal to distances $D_6$ and $D_5$. The photocurrent produced by photodetector 43L is relatively high compared to the photocurrent produced by photodetector 43R.

The relative relationship between the received photocurrent signals, $P_L$ and $P_R$, (from photodetectors 43L and 43R, respectively) and the required current amplitudes of the current signals to the electrodes, $A_L$ and $A_R$, can be summarized in the following table for the four extreme positions of the spinal cord in the spinal canal.

TABLE 1

| Position | $P_L$ | $P_R$ | $A_L$ | $A_R$ |
| --- | --- | --- | --- | --- |
| Front—0° | L | L | H | H |
| Right—90° | L | H | H | L |
| Back—180° | H | H | L | L |
| Left—270° | H | L | L | H |

Optical ratios associated with each photodetector pair correlate to a function of spinal cord position as determined ratiometrically (for side-to-side movement) and proportionally (for front-to-back movement) to the detected light intensities.

The ratio of the current signals from photodetector 43L and photodetector 43R is representative of spinal position left to right.

$$r = \frac{P_L}{P_R} \quad (3)$$

The intensity of the photocurrent signals is representative of spinal position front to back. The total intensity can be represented by:

$$I = P_L + P_R \quad (4)$$

Figure 7:
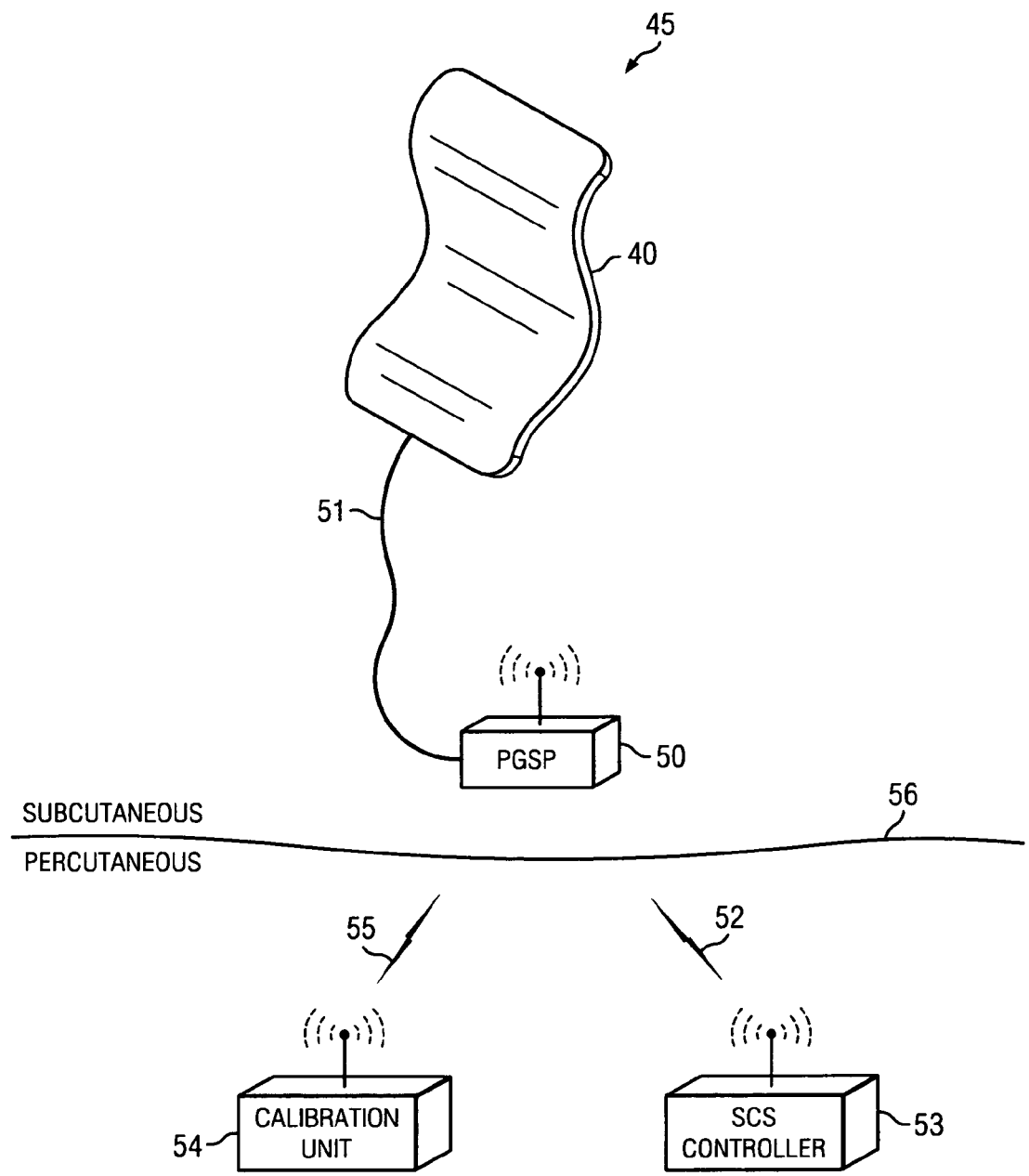
FIG. 7 shows a schematic representation of a preferred embodiment of the positionally sensitive spinal cord stimulation system.

Referring to FIG. 7, a preferred embodiment of the implanted components of the system is described. Spinal cord stimulator 45 includes pulse generator and signal processor (PGSP) 50 and electrode assembly 40. Main lead 51 connects electrode assembly 40 to PGSP unit 50. PGSP unit 50 provides power to the electrodes and the IR emitter and houses the electrical components of the system. PGSP unit 50 gathers and processes photodetector signals and makes adjustments to the electrode current (or voltage) based on the photodetector signals. PGSP unit 50 is connected by wireless communication link 52 across skin boundary 56 to SCS controller 53. The SCS controller is configured to allow activation of and adjustments to PS-SCS stimulator percutaneously. PSGP unit 50 is also connected by wireless communication link 55 to calibration unit 54. Calibration unit 54 is programmed to accept patient feedback and transmit it to PGSP 50 during calibration.

Figure 8A:
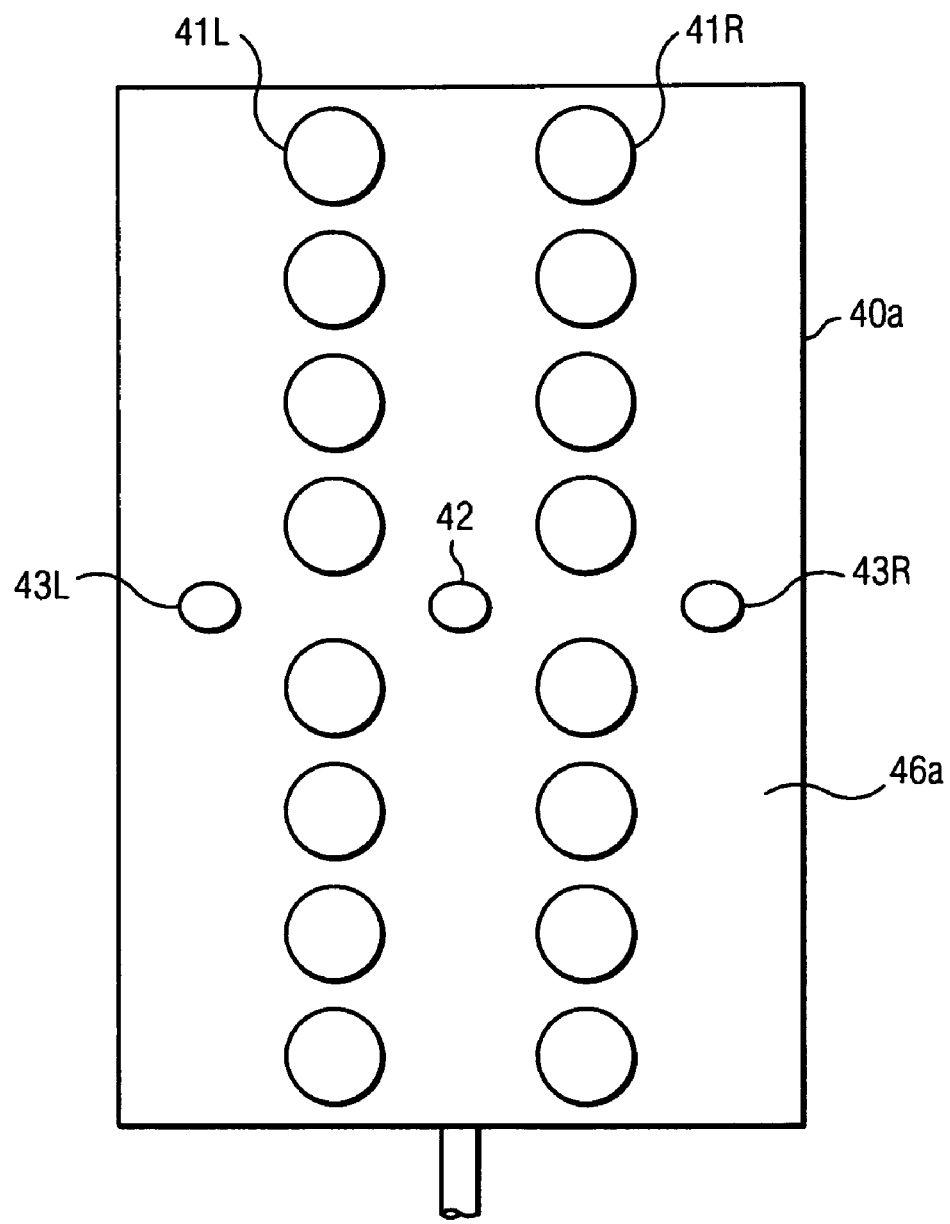
FIGS. 8a and 8b show two preferred embodiments of an electrode assembly.

Referring to FIG. 8a, a first preferred embodiment of electrode assembly 40a will be described. IR emitter 42 is centrally positioned in elastomeric housing 46a. A vertical linear array of electrodes, 41L and 41R, are positioned to each side of the IR emitter. Photodetectors 43L and 43R are positioned to the left and right of the arrays of electrodes 41L and 41R, respectively, and in horizontal alignment with the IR emitter. Each electrode has a separate electrical conductor in a set of electrode leads contained in main lead 51 so that the current to each contact may be independently controlled. The components of the electrode assembly are sealed in elastomeric housing 46a.

Figure 8B:
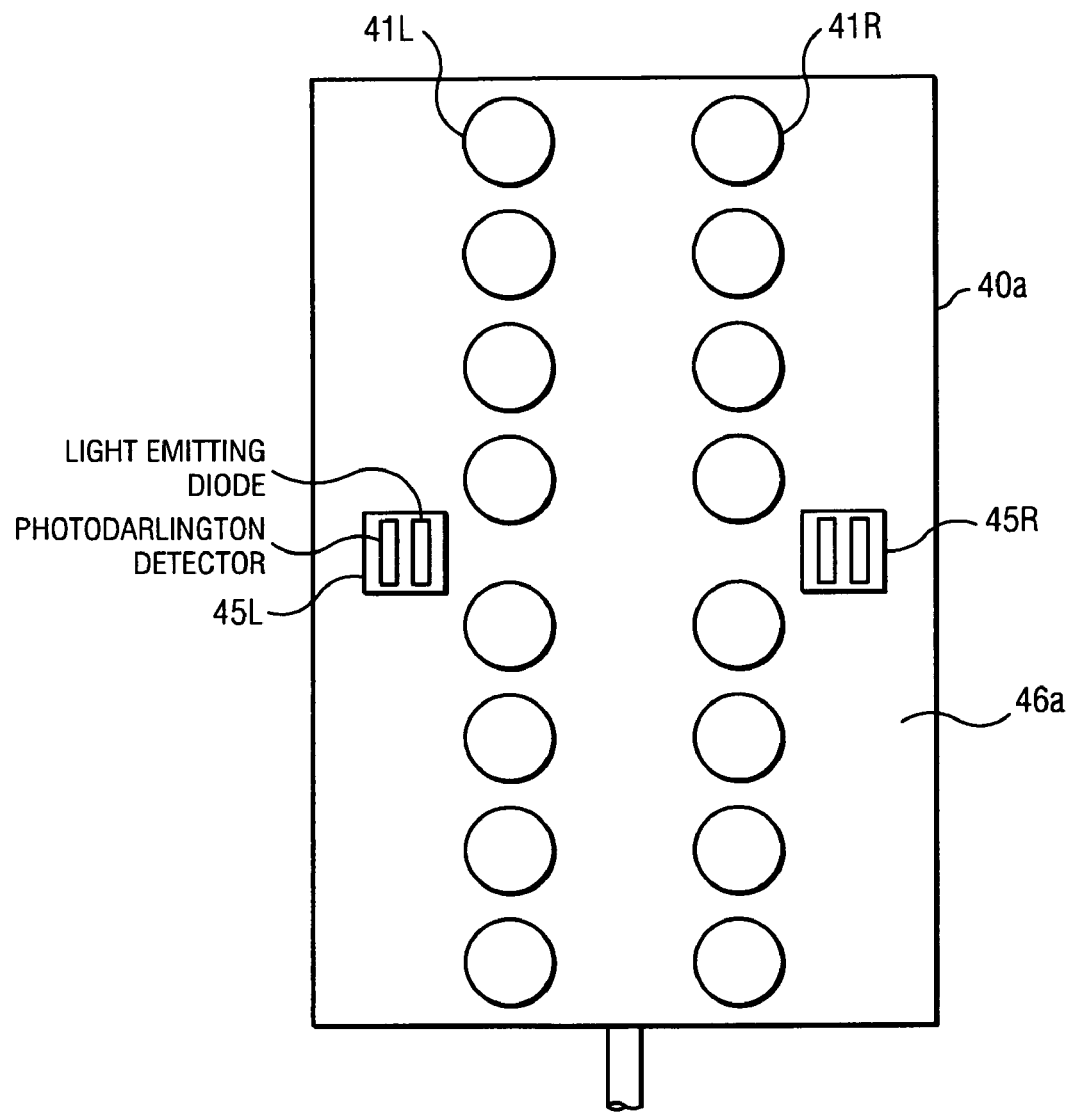

Referring to FIG. 8b, a second preferred embodiment of electrode assembly 40a will be described. A vertical linear array of electrodes, 41L and 41R, are positioned to each side of the IR emitter. An IR emitter and photodetector are packaged into a single integrated device as an IR emitter/detector pair. IR emitter/detector pair 45L and IR emitter/detector pair 45R are positioned to the left and right of the arrays of electrodes 41L and 41R, respectively. Each electrode has a separate electrical conductor in a set of electrode leads contained in main lead 51 so that the current to each contact may be independently controlled. The components of the electrode assembly are sealed in elastomeric housing 46a. FIG. 8B indicates the physical locations of the IR emitter/detector pairs to be slightly outside of the array of electrodes. In alternate embodiments, the IR emitter detector pairs may be located in line with the electrode array or inside of the electrode array. In another alternate embodiment, a central IR emitter/detector pair may be situated in between the left and right IR emitter/detector pairs.

A suitable single integrated device comprising a photoemitter and a photodarlington detector is part number OPB707A from Optek Technology, Inc.

Figure 9:
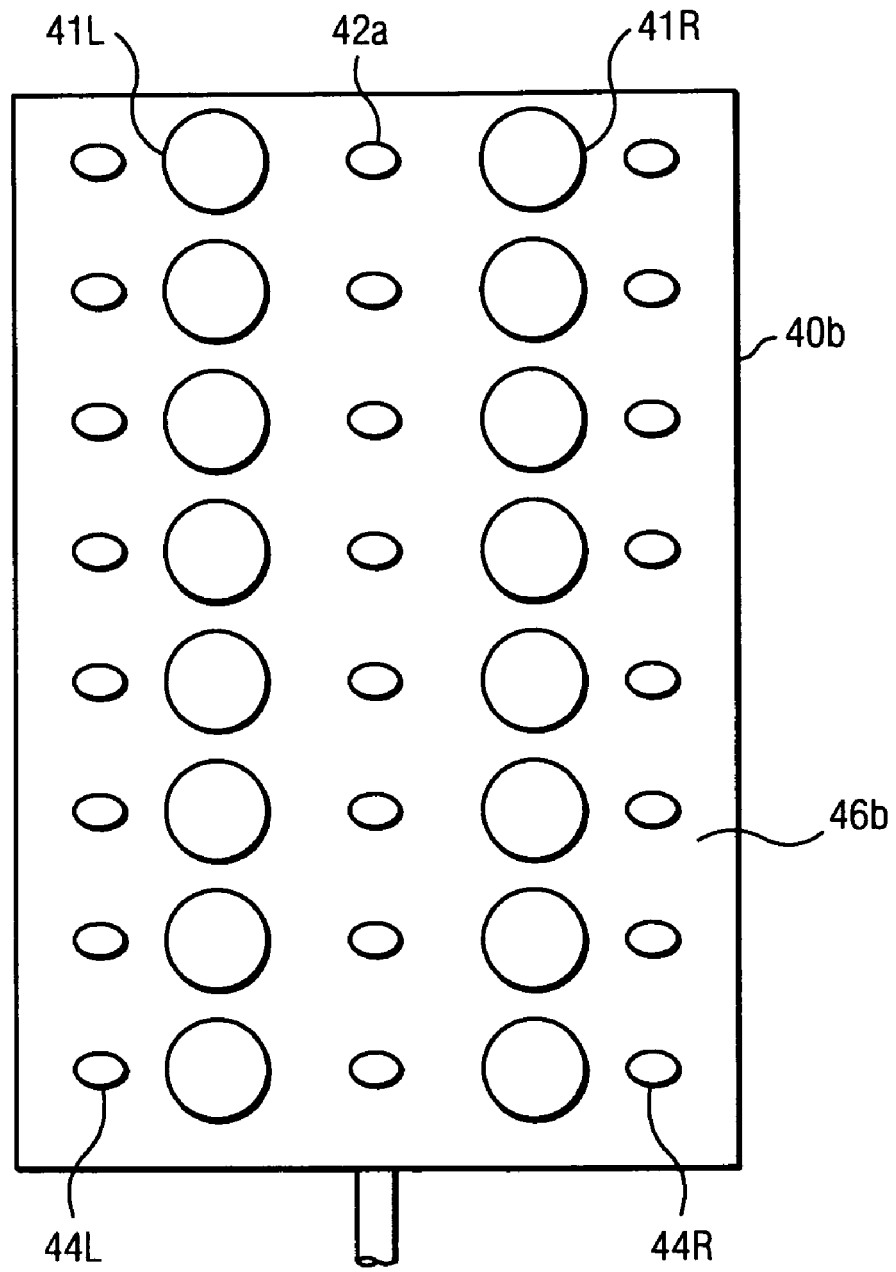
FIG. 9 shows an alternate embodiment of an electrode assembly.

FIG. 9 shows an alternate embodiment of electrode assembly 40b. Electrode assembly 40b includes two sets of electrodes 41L and 41R, a linear set of IR emitters 42a and two sets of IR photodetectors 44L and 44R. Set of IR emitters 42A are preferably located in a vertical line near the center of the elastomeric housing. The sets of electrodes are positioned in vertical rows to each side of the IR emitters. The number of electrodes may vary depending on the dimensions of the elastomeric housing. IR photodetectors 44L and 44R positioned to each side of the two sets of electrodes. Each electrode has a separate electrical conductor in a set of electrode leads contained in main lead 51 so that the current to each contact may be independently controlled. The components of the electrode assembly are sealed into the elastomeric housing 46b.

Figure 10:
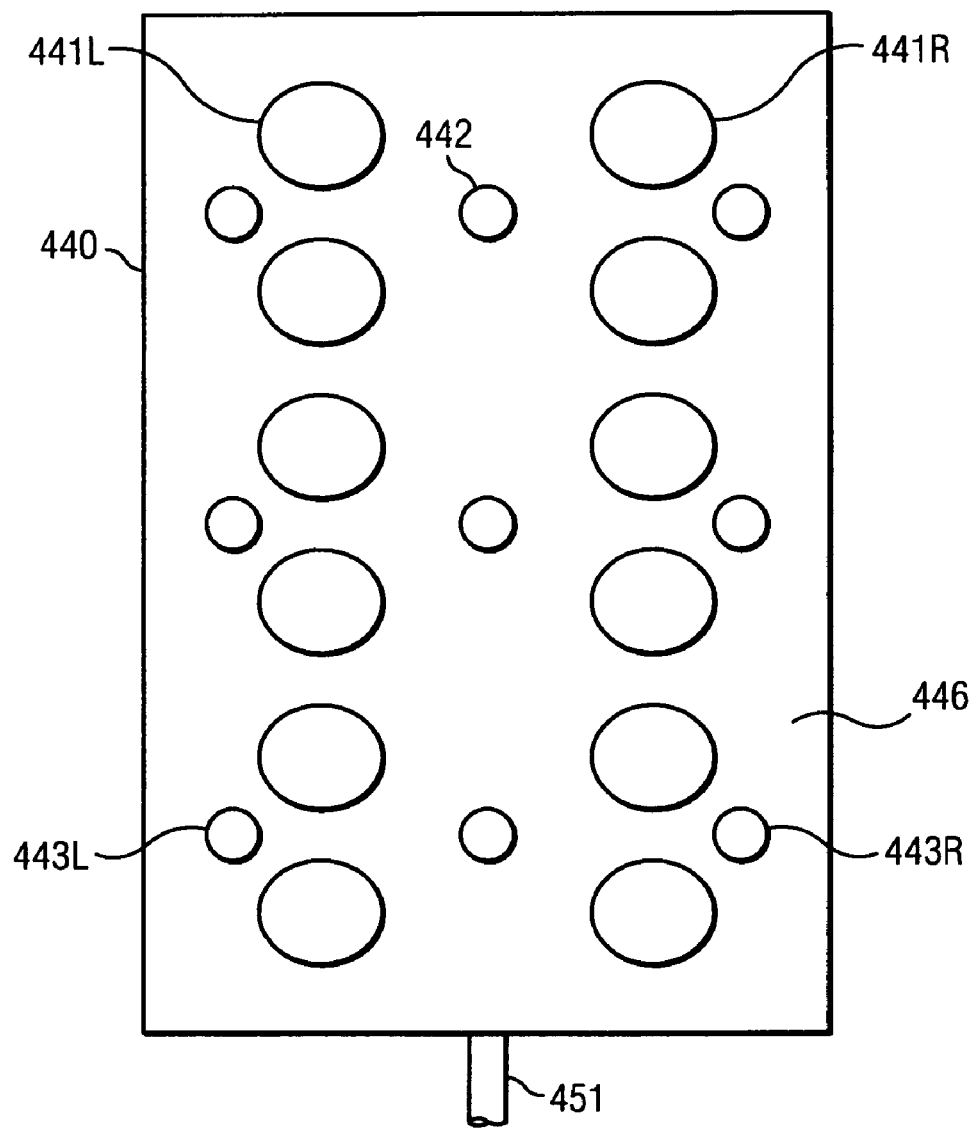
FIG. 10 shows an alternate embodiment of an electrode assembly.

FIG. 10 illustrates an alternate embodiment of electrode assembly 440. Electrode assembly 440 includes two sets of electrodes 441L and 441R, a set of optical lenses 442 for light delivery, optical lenses 443L and optical lenses 443R for light collection. Optical fibers are terminated in each of the lenses and routed into main lead 451. Optical lenses 442 act to direct light from the optical fibers toward the spinal cord uniformly. In the preferred embodiment, the lenses are Fresnel lenses which reduce the profile depth of the elastomeric housing and diffuse light uniformly. Optical lenses 443L and 443R act as collectors to efficiently gather and collimate light received. Each electrode is provided a separate electrical conductor in main lead 451 so that the current to each electrode may be independently controlled.

PGSP unit 50 is preferably powered by batteries. In an alternate embodiment, PGSP unit 50 derives power from capacitive or inductive coupling devices. Calibration may further calibrate the batteries, the capacitive devices, or inductive coupling in PGSP unit 50. Communication links 52 or 55 may further serve as a means of providing electrical charge for the batteries or capacitive devices of PGSP unit 50.

Figure 11A:
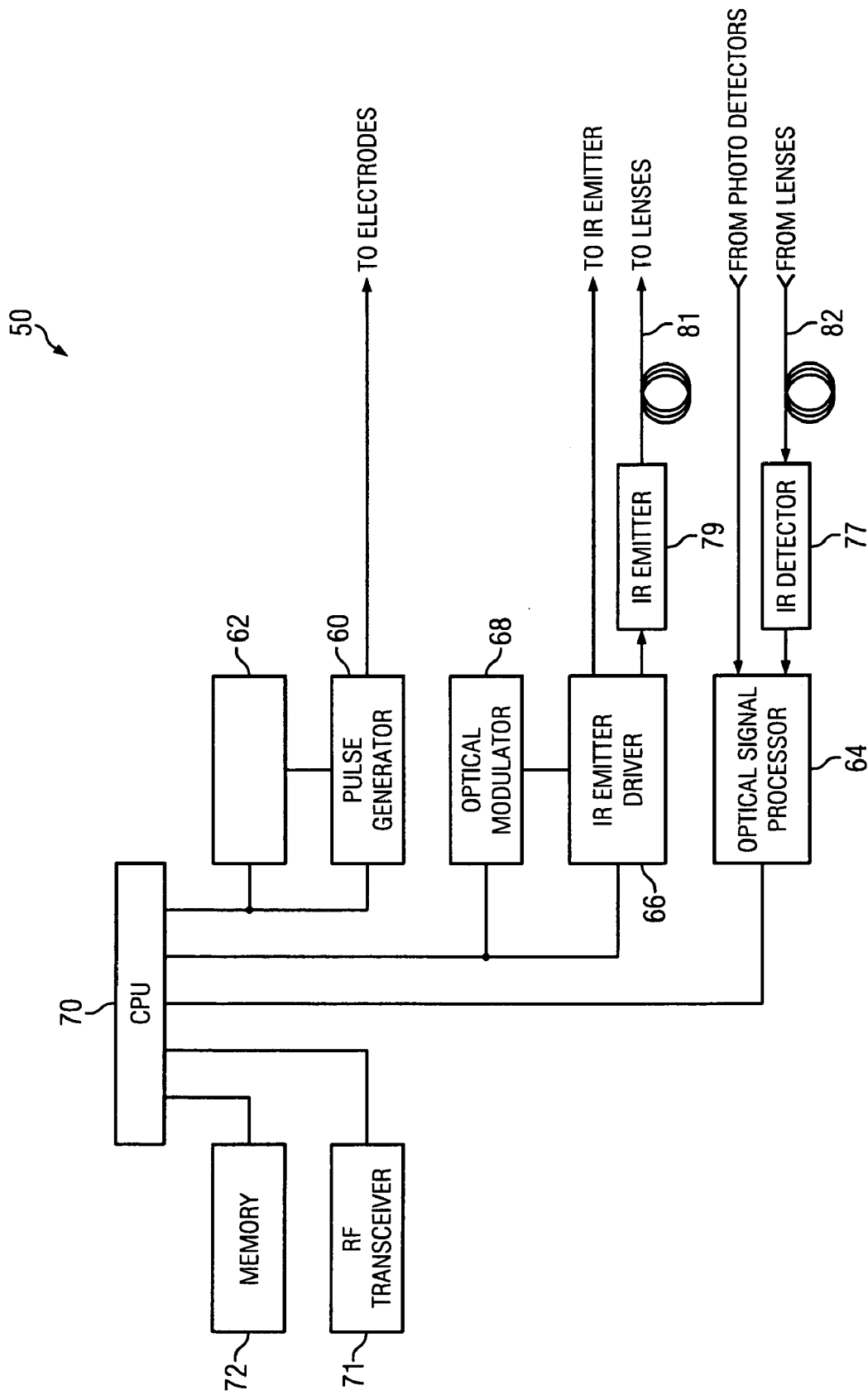
FIG. 11a is a block diagram of the components of a preferred embodiment of a pulse generation and optical signal processing unit.

Referring to FIG. 11a, PSGP unit 50 will be described. PSGP unit 50 comprises CPU 70 including onboard memory 72. CPU 70 is connected to pulse modulator 62 and pulse generator 60. Modulator 62 is also connected to pulse generator 60. CPU 70 is also operatively connected to optical modulator 68 and optical signal processor 64. Optical modulator 68 is connected to infrared emitter driver 66. Infrared emitter driver 66 is connected to the IR emitter in the electrode assembly.

IR emitter driver 66 is also connected to IR emitter 79. In embodiments which require fiber optic connection, infrared emitters 79 include appropriate lenses and connectors to effectively couple IR emitter 79 to fiber 81. Fiber 81 is connected to light delivery lenses in the electrode array.

CPU is also connected to optical signal processor 64. Optical signal processor 64 is connected to the set of photodetectors in electrode assembly 40. Pulse generator 60 is connected to the set of electrodes in electrode assembly 40.

In order to generate a pulse to the electrodes, the CPU consults a calibration table stored in onboard memory 72 to determine pulse width $P_W$, pulse frequency $P_f$ and pulse amplitudes $A_L$ and $A_R$ for the left and right electrodes, respectively. The pulse width and frequency are transmitted to pulse modulator 62 which creates a modified square wave signal. The modified square wave signal is passed to pulse generator 60. CPU 70 passes the amplitude for the left and right electrodes to pulse generator 60 in digital form. Pulse generator 60 then amplifies the modified square wave according to $A_L$ and $A_R$ to form left and right modified square wares and transmits them to the left and right electrodes, respectively.

The stimulation waveform of the preferred embodiment is a modified square wave having an amplitude and duration (or width). Pulse widths varying from 20 to 1000 microseconds have been shown to be effective. The frequency of the pulse waveforms between 20 and 120 hertz have been shown to be effective. The output amplitude is preferably from 0(zero) to +/−20 mA or 0(zero) to +/−10 V but may vary beyond those ranges according to patient sensitivity.

Optical signal processor 64 receives signals from the set of photodetectors, filters the optical signals, and correlates the optical signals to the IR emitter amplitude, pulse width and frequency. Optical signal processor 64 may include a synchronized gated detection (e.g. lock-in amplifier type) function or other demodulation function to improve the signal to noise ratio of the detected light.

IR detector 77 is connected to optical signal processor 64. IR detector 77 translates incoming light pulses from fiber 82 into electrical signals processed by optical signal processor 64. IR detector 77 includes lenses to couple IR detector 77 to fiber 82. Sensitivity of the set of IR photodetectors is similar to that of part APA3010P3Bt from Kingbright Corporation.

CPU 70 is connected to optical modulator 68. Optical modulator 68 generates the IR emission waveform transmitted to the IR emitters according to parameters set and transmitted by CPU 70. IR emitter driver 66 is connected to both optical modulator 68 and CPU 70. In operation, to send an IR light pulse, the CPU activates the optical modulator to generate the appropriate waveform which is then transmitted to the IR emitter driver. The IR emitter driver transmits the waveform to the IR emitters. If IR emitter 79 is used, the pulse is launched into fiber 81.

The IR emission waveform set by CPU 70 may take several forms. For example, IR emitter pulse width may be very short to minimize power consumption. A single IR emitter pulse may occur for a set of electrode stimulation pulses. Typical wavelength of the IR light from the set of IR emitters is 940 nm. Typical output intensity of the IR emitters is 1 to 2 mW and a suitable part is part # PDI-E900 from Advanced Photonix, Inc.

CPU 70 is in transcutaneous communications, via RF transceiver 71, with calibration and programming unit 54 and SCS controller 53.

Figure 11B:
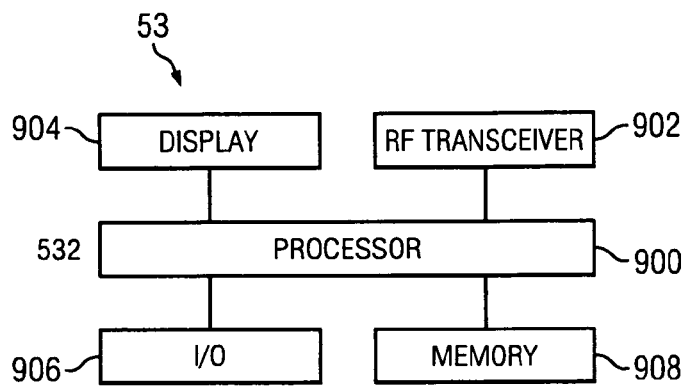
FIG. 11b is a block diagram of the components of a preferred embodiment of an SCS controller.

Referring to FIG. 11*b*, SCS controller 53 will be described. SCS controller 53 includes processor 900 connected to RF transceiver 902, display 904, input/output device 906, and memory 908. In the preferred embodiment, display 904 is a low power liquid crystal display adapted to show the current operational state of the system. I/O device 906 is a simple push button contact array which is constantly monitored by processor 900. Memory 908 is onboard memory connected to processor 900. In the preferred embodiment, RF transceiver 902 is a low power transmitter/receiver combination.

Figure 11C:
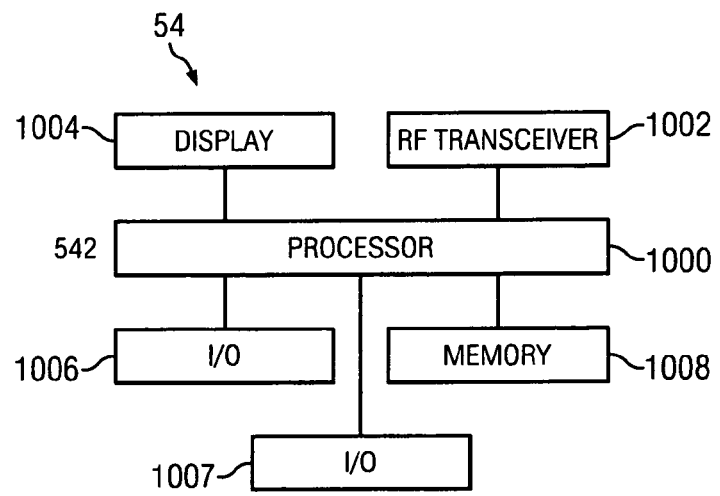
FIG. 11c is a block diagram of the components of a preferred embodiment of a calibration and programming unit.

Referring to FIG. 11*c*, calibration and programming unit 54 will be described. Calibration and programming unit 54 includes processor 1000 connected to onboard memory 1008, input/output devices 1006 and 1007, RF transceiver 1002 and display 1004. Display 1004, in the preferred embodiment, is a low power liquid crystal display. Input/output device 1006 and input/output device 1007 are simple push button switches monitored continuously by the processor. Memory 1008 is onboard processor 1000. RF transceiver 1002 is a low power transmitter/receiver combination.

Referring to FIGS. 12*a*, 11*a*, 11*b* and 11*c*, method 80 of operation of the PS-SCS stimulator will be described. In the preferred embodiment, method 80 takes the form of a computer program which is resident in memory 72 of CPU 70 of PGSP 50. When activated, the program forms a continuous cycle. At step 81, RF transceiver 71 is continually polled for a change of operation code signal to be received from SCS controller 53. One of three options is always present, "start?", "calibrate?" and "stop?".

At step 83, if operation change code "start?" is received, the method moves to step 92. At step 92, CPU 70 activates optical modulator 68, which in turn activates IR emitter driver 66 to generate a set of current pulses sent to the IR emitters. At step 93, the resultant current levels at the photodetectors, $PD_L$ and $PD_R$, are measured by optical signal processor 64 and passed to CPU 70. At step 95, CPU estimates the amplitude $A_L$ and $A_R$ of the a train of pulses to be sent to the electrodes. At step 99, optionally, the CPU sets the values of the pulse width $P_W$ and frequency $P_f$ of the pulse train to be sent to the electrodes. At step 152, the CPU activates the pulse modulator to create the waveform of the pulse train to be sent to the electrodes and activates pulse generator 60 to generate the pulse train. At step 154, the CPU stores the values of $PD_L$, $PD_R$, $A_L$, $A_R$, $P_W$ and $P_f$ in memory for future retrieval. The method then returns to step 81.

If at step 83, the operation change code is not "start?", the method proceeds to step 85. At step 85, the CPU determines if the operation change code is "calibrate?". If so, the method moves to step 87. At step 87, the CPU transmits the history log stored in memory to calibration unit 55. At step 89, the CPU enters the calibration routine as will be described more fully later. The method then returns to step 81.

If at step 85, the operation change code is not "calibrate?", the method moves to step 91. At step 91, the CPU determines if the operation change code is "stop?". If so, the method returns to step 81. If not, the method proceeds to step 92 and continues as previously described.

In the preferred embodiment, the pulse width and frequency is kept constant for a given patient and only the left and right electrode amplitudes are varied.

Figure 12A:
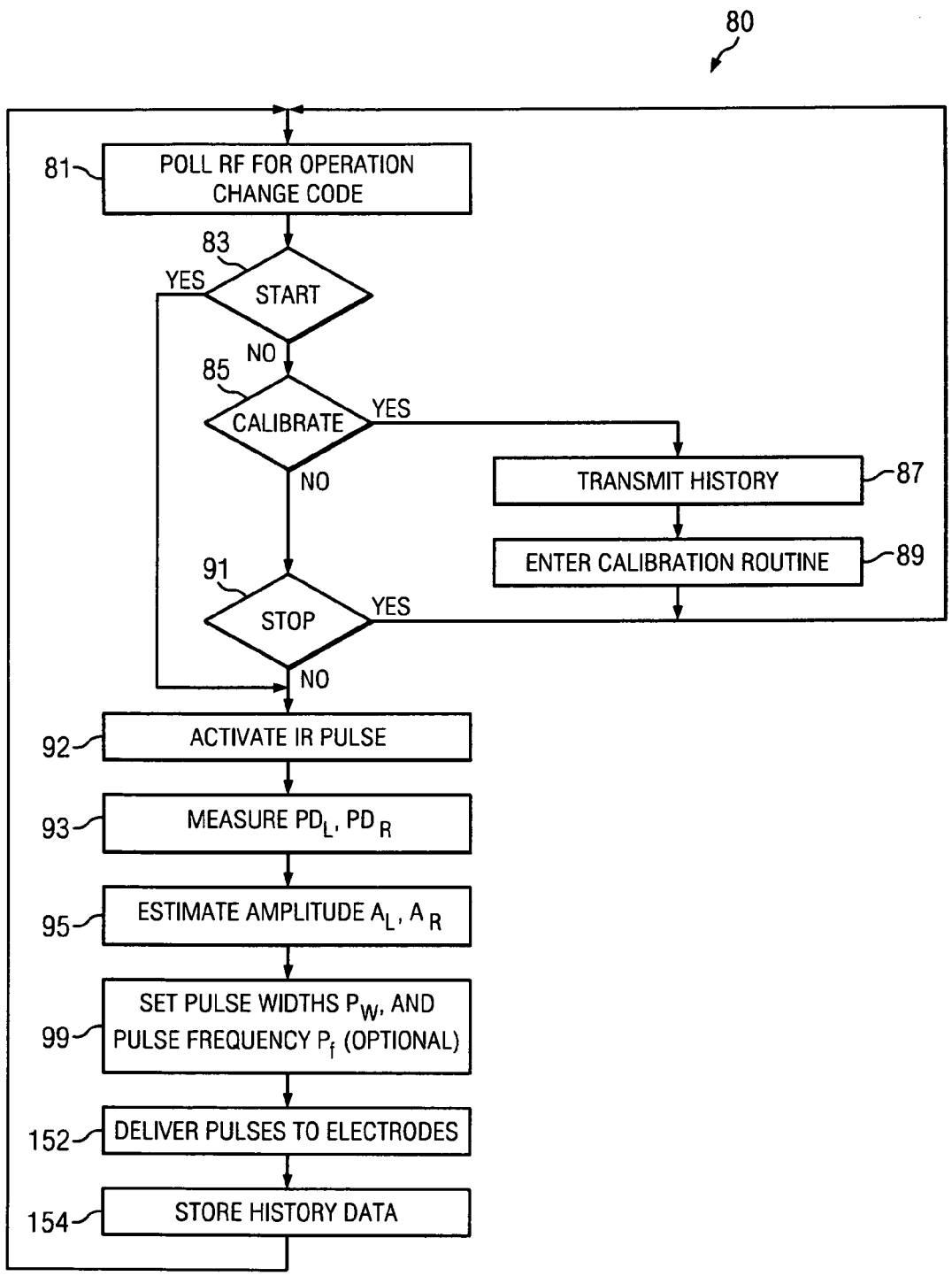
FIGS. 12a through 12d are flow diagrams of a method of operation of a preferred embodiment.
Figure 12B:
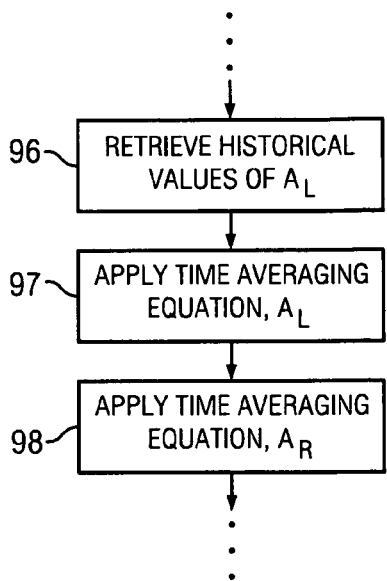

Referring to FIG. 12*b*, an alternate embodiment of estimating amplitude values, at step 95 will be described. In this embodiment, the CPU time averages historical amplitudes $A_L$ and $A_R$ to arrive at the estimated electrode amplitudes. At step 96, the CPU obtains a set of historical values for $A_L$ and $A_R$ and a predetermined weighting value from memory.

At step 97, the following equation is applied:

$$A_L(\text{delivered}) = \frac{w_k \cdot A_L(k) + w_{k-1} \cdot A_L(k-1) + w_{k-2} \cdot A_L(k-2) + \ldots}{w_k + w_{k-1} + w_{k-2} + \ldots} \quad (5)$$

where:
$w_k$=predetermined weight for the values of $A_L$ at the current time $A_L(k)$ and earlier times $A_L(k-1)$, $A_L(k-2)$, . . . . At time k;
$A_L$=left electrode amplitude; and,
At step 98, the following equation is applied:

$$A_R(\text{delivered}) = \frac{w_k \cdot A_R(k) + w_{k-1} \cdot A_R(k-1) + w_{k-2} \cdot A_R(k-2) + \ldots}{w_k + w_{k-1} + w_{k-2} + \ldots} \quad (6)$$

where:
$w_k$=predetermined weight for the values of $A_R$ at the current time $A_R(k)$ and earlier times $A_R(k-1)$, $A_R(k-2)$, . . . . At time k;
$A_R$=right electrode amplitude.

Figure 12C:
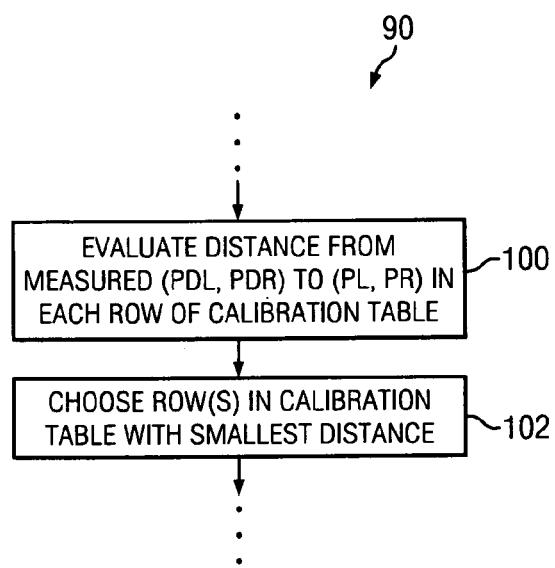

Referring to FIG. 12c, an alternate method of estimating amplitude values at step 95 will be described.

At step 100, the CPU computes a distance factor dP according to the equation:

$$dP = \sqrt{(PD_L - P_L)^2 + (PD_R - P_R)^2} \quad (7)$$

where:
$PD_L$=measured value of left photodetector current;
$PD_R$=measured value of right photodetector current;
$P_L$=calibration table value of left photodetector current; and
$P_R$=calibration table value of right photodetector current.

dP is calculated for each row corresponding to patient positions 1-4 of the calibration table. At step 102, the values $A_L$ and $A_R$ are estimated as those that correspond to the row of the calibration table having the smallest distance factor dP.

Figure 12D:
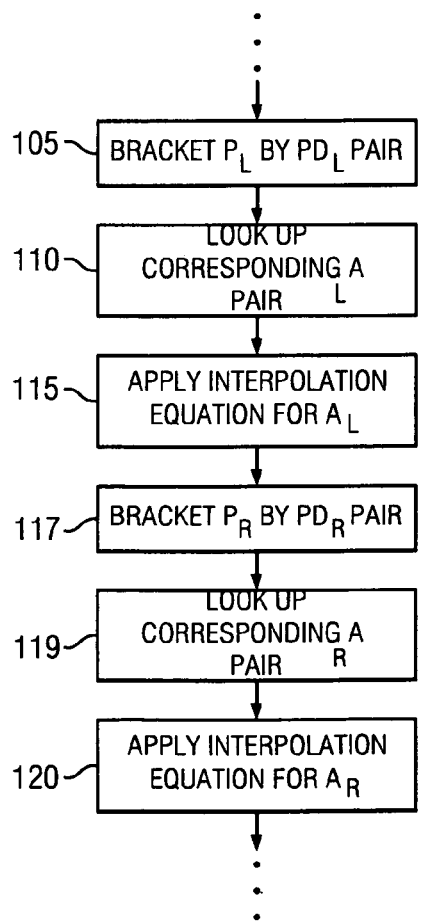

Referring to FIG. 12d, an alternate method of estimating amplitude values, step 95, will be described.

At step 105, the CPU consults the calibration table to locate the closest pair of consecutive $PD_L$ values that bracket the measured value $P_L$, $[PD_{L\ TOP}, PD_{L\ BOTTOM}]$. At step 110, the CPU locates the pair of $A_L$ values that correspond to the closest pair of $PD_L$ values, $[A_{L\ TOP}, A_{L\ BOTTOM}]$. At step 115, the CPU applies the interpolation equation to locate the estimated value of $A_L$, as follows:

$$A_L = \left(\frac{(A_{L\ TOP} - A_{L\ BOTTOM})}{(PD_{L\ TOP} - PD_{L\ BOTTOM})}\right) \cdot (P_L - PD_{L\ BOTTOM}) + A_{L\ BOTTOM} \quad (8)$$

where:
$A_L$=estimated value of the left electrode pulse current;
$PD_{L\ TOP}$=upper bracketed value of photodetector current from the calibration table;
$PD_{L\ BOTTOM}$=lower bracketed value of the photodetector current from the calibration table;
$A_{L\ TOP}$=upper value of the electrode pulse current from the calibration table corresponding to $PD_{L\ TOP}$;
$A_{L\ BOTTOM}$=lower value of the pair of electrode amplitudes from the calibration table corresponding to $PD_{L\ BOTTOM}$.

At step 117, the CPU consults the calibration table to locate the closest pair of consecutive $PD_R$ values that bracket the measured value $P_R$, $[PD_{R\ TOP}, PD_{R\ BOTTOM}]$. At step 119, the CPU locates the pair of $A_R$ values that correspond to the closest pair of $PD_R$ values, $[A_{R\ TOP}, A_{R\ BOTTOM}]$. At step 120, the CPU applies the interpolation equation to locate the estimated value of $A_R$, as follows:

$$A_R = \left(\frac{(A_{R\ TOP} - A_{R\ BOTTOM})}{(PD_{R\ TOP} - PD_{R\ BOTTOM})}\right) \cdot (P_R - PD_{R\ BOTTOM}) + A_{R\ BOTTOM} \quad (9)$$

where:
$A_R$=estimated value of the right electrode pulse current;
$PD_{R\ TOP}$=upper bracketed value of photodetector current from the calibration table;
$PD_{R\ BOTTOM}$=lower bracketed value of photodetector current from the calibration table;
$A_{R\ TOP}$=upper value of the electrode pulse current from the calibration table corresponding to $PD_{R\ TOP}$;
$A_{R\ BOTTOM}$=lower value of the pair of electrode amplitudes from the calibration table corresponding to $PD_{R\ BOTTOM}$.

Referring to FIG. 12a, in the preferred embodiment, pulse width and frequency is kept constant for a given patient and only the left and right electrode amplitudes are varied. In an alternate embodiment, step 150 is performed whereby pulse width and pulse frequency are varied according to the calibration values stored in the calibration table for each electrode.

Figure 13A:
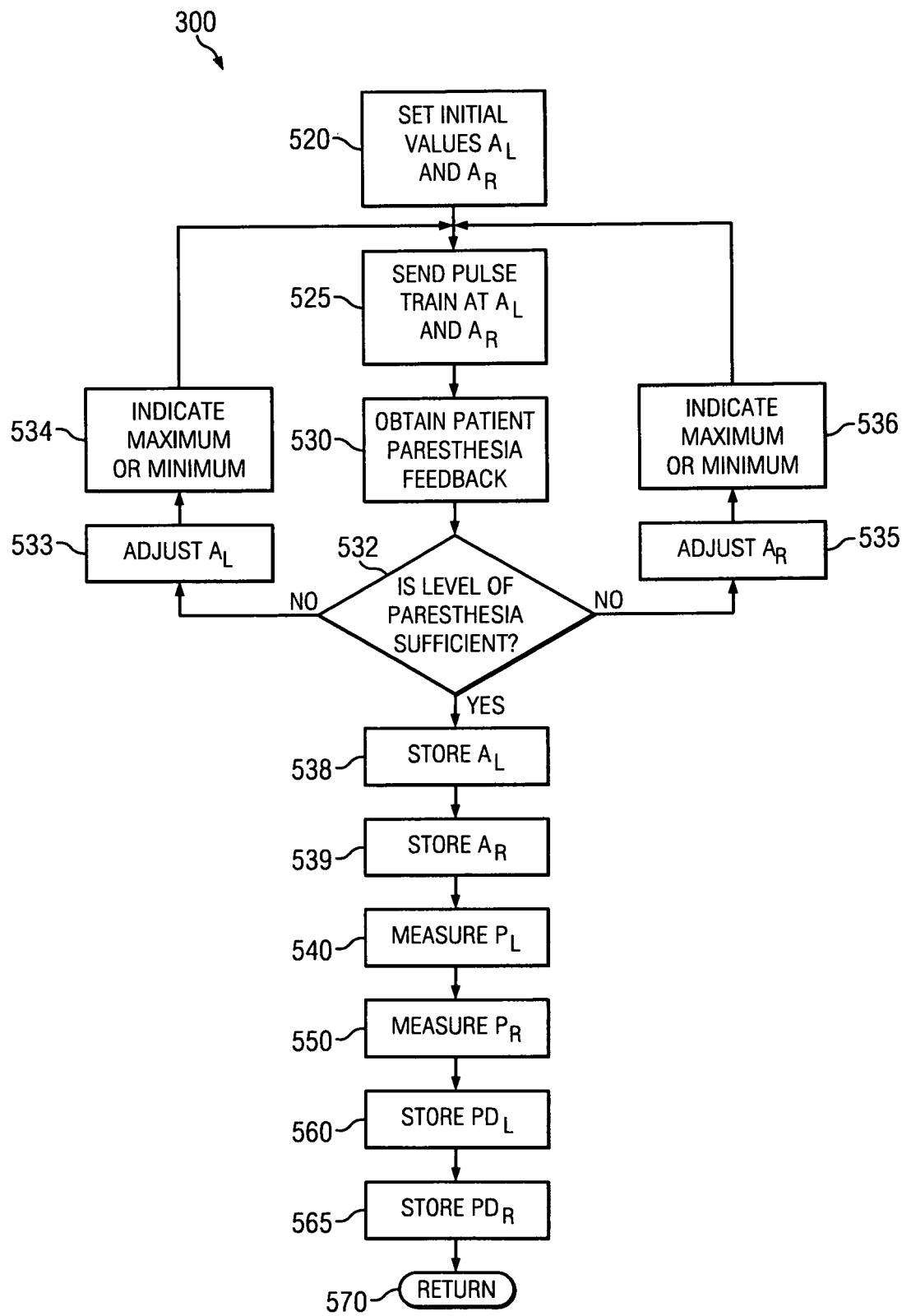
FIGS. 13a through 13c are flow diagrams of a method of calibrating a preferred embodiment.
Figure 13B:
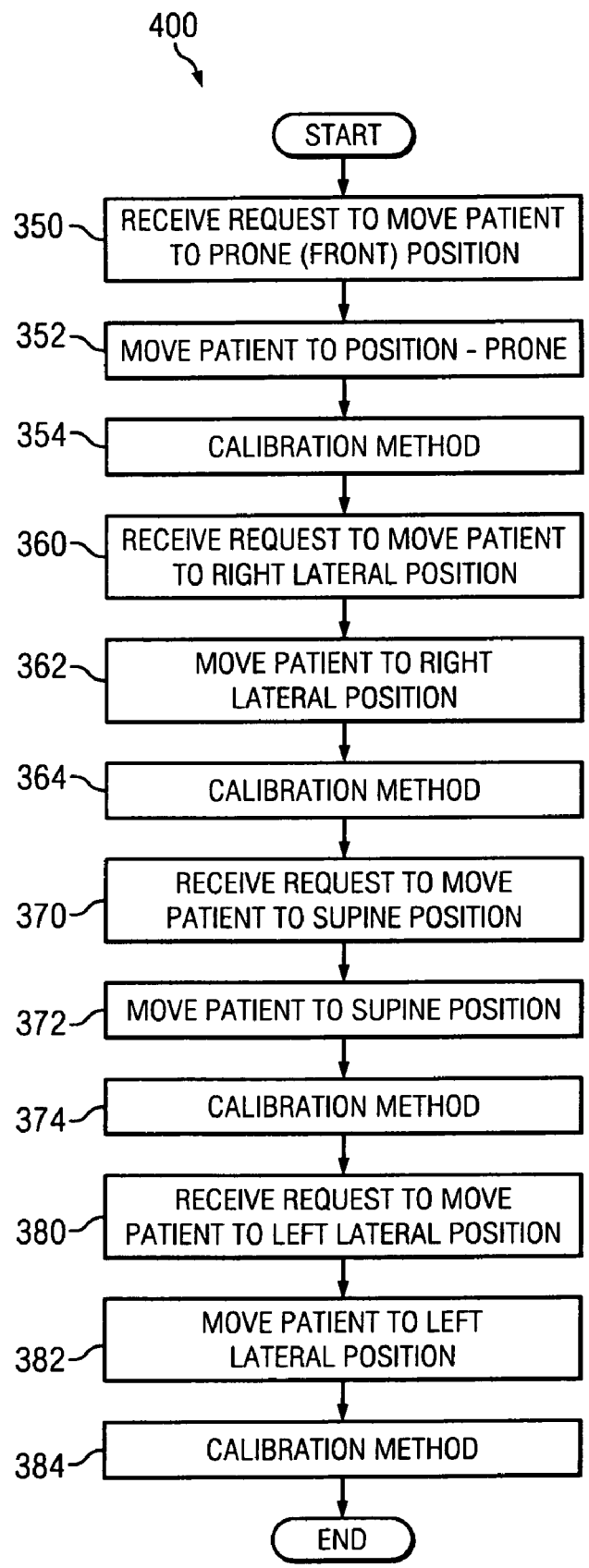

Referring to FIGS. 13a and 13b, a method of calibration of the SCS stimulator will be described.

Referring to FIGS. 13a, 11a and 11c, the processor is programmed to carry out steps of calibration method 300 upon request by a calibration control program. At step 520, the levels of $A_L$ and $A_R$ are set at the minimum value of a predetermined range for each. At step 525, the pulse generator is directed by the CPU to send a train of pulses to each of the left and right electrodes at the minimum levels of $A_L$ and $A_R$, respectively. At step 530, paresthesia perception feedback is solicited from the patient.

If the level of parasthesia is not optimal according to the patient feedback, then the method moves to step 532. At step 532, the processor monitors the input/output devices to determine if $A_L$, $A_R$ or both $A_L$ and $A_R$ need to be adjusted, or if the level of paresthesia is sufficient. If $A_L$ needs to be increased or decreased from the current level, then the value of $A_L$ is adjusted by a discrete amount in step 533. If the level of $A_L$ is at a maximum or a minimum level, an alert is made by the calibration and programming unit in step 534. If $A_R$ needs to be increased or decreased from the current level, then the value of $A_R$ is adjusted by a discrete amount in step 535. If the level of $A_R$ is at a maximum or a minimum level, an alert is made by the calibration and programming unit in step 536. The alert in step 534 and step 536 may be a visual indication, audio indication or both visual and audio indication.

After adjustment, the step 525 is repeated, and a train of pulses is delivered to each electrode at the new levels $A_L$ and $A_R$. At step 530, patient paresthesia feedback is again solicited. If the level of paresthesia is still not optimal according to the patient feedback, the method repeats steps 533, 534, 535 and 536 as required. If the level of paresthesia is sufficient according to patient feedback at step 532, the method moves to step 538.

At step 538, the CPU stores the value $A_L$. At step 539, the CPU stores the value of $A_R$. At step 540, the CPU measures the optical signal feedback from the optical signal processor representative of the current from the left photodetector $P_L$. At step 550, the CPU measures the optical feedback signal from the optical signal processor representative of the current from the right photodetector $P_R$. At steps 560 and 565, the CPU stores $P_L$ and $P_R$ in the calibration table. At step 570, the calibration method steps complete by returning control to the calibration control program.

Referring to FIGS. 13b and 11c, the processor of calibration unit 54 is programmed to further carry out the following method steps for a calibration control program 400 in cooperation with physical motion of the patient.

At step 350, RF transceiver 1002 receives a signal indicative of a request to move the patient to a prone position and passes it to processor 1000. At step 352, the patient is positioned in a prone position. Calibration method 300, as described in FIG. 13a, is carried out to maximize the level of paresthesia experienced by the patient.

At step 360, RF transceiver 1002 receives a signal indicative of a request to move the patient to a right lateral position and passes it to processor 1000. At step 362, the patient is positioned in a right lateral position. Calibration method 300 is then carried out to optimize the level of paresthesia experienced by the patient.

At step 370, RF transceiver 1002 receives a signal indicative of a request to move the patient to a supine position and passes it to processor 1000. At step 372, the patient is positioned in a supine position. Calibration method 300 is then carried out to optimize the level of paresthesia experienced by the patient.

At step 380, RF transceiver 1002 receives a signal indicative of a request to move the patient to a left lateral position and passes it to processor 1000. At step 382, the patient is positioned in a left lateral position. Calibration method 300 is then carried out to optimize the level of paresthesia experienced by the patient.

After steps 380, 382 and 300 finish, the calibration program is complete.

The order of patient positions in calibration program 400 may be changed in alternative embodiments. Additional patient positions may be added to calibration program 400 in alternative embodiments, for example, the patient may be rotated clockwise to calibrate a level of paresthesia required for a clockwise position.

Figures 13C, 14:
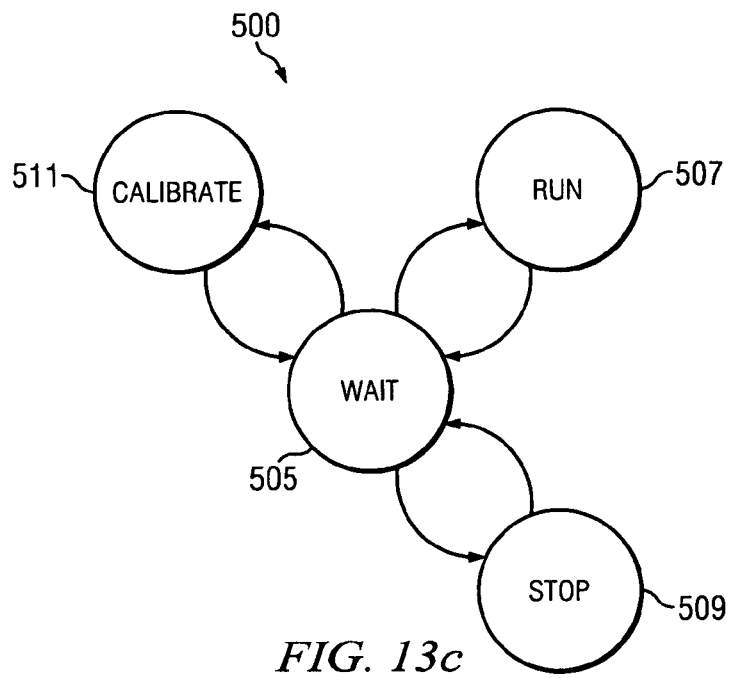
FIG. 14 is a graphic representation of a calibration table.

Referring to FIGS. 13c and 11b, the various states of the SCS controller will be described. At state 505, SCS controller 53 enters a waiting posture and continually polls I/O unit 906. Upon receipt, processor 900 enters run state 507 and transmits a "run" signal to RF transceiver 902. RF transceiver then transmits the "run" signal to PGSP 50 for further action. After transmission, the processor returns to wait state 505.

If a "stop" signal is received from I/O device 906, processor 900 passes a signal to RF transceiver 902, which in turn sends the signal to PGSP 50. The processor then returns to wait state 505.

If a "calibrate" signal is received from I/O unit 906, at step 511, processor 900 transmits a "calibrate" signal to RF transceiver 902, which in turn sends the signal to PGSP 50. Processor 900 then returns to wait state 505.

FIG. 14 shows a calibration table 1150 for the preferred embodiment. Each row is a record for the optimal electrode settings for a patient position for a specific pair of electrodes in the electrode assembly. Calibration table 1150 includes seven columns, patient position identifier 1152, left photodetector value $PD_L$ 1154, right photodetector value $PD_R$ 1156, left electrode stimulation pulse amplitude $A_L$ 1158, right electrode pulse amplitude $A_R$ 1160, electrode stimulation pulse width $P_W$ 1161, and electrode pulse frequency $P_f$ 1162.

Patient position identifier 1152 in a preferred embodiment includes four positions, front (prone—0°), right—90°, back (supine—180°) and left—270°. Each row in Table 1150 is associated with one of the four patient positions. Left electrode stimulation pulse amplitude 1158 and right electrode stimulation pulse amplitude 1160 are values which are derived during calibration and recorded for different spinal cord positions, corresponding to the patient position. In the preferred embodiment, the left electrode stimulation pulse amplitude 1158 and right electrode stimulation pulse amplitude 1160 are directly proportional to the stimulation energy delivered to the respective electrodes.

In alternate embodiments, calibration may be performed for additional physical positions such that additional rows are placed in table 1150.

Left photodetector value $PD_L$ 1154 is the measured intensity for the left photodetector. Right photodetector value 1156 is the measured intensity for the right photodetector.

Electrode stimulation pulse width 1161 and frequency 1162 are each constant. However, in an alternate embodiment, electrode stimulation pulse width 1161 and electrode pulse frequency 1162 are varied through a predetermined range during calibration and recorded for each patient position.

The method 80 of FIG. 12a can be extended to those SCS electrode assemblies that contain more than one pair of photodetectors. Stimulation energy can be delivered in different regions of the spinal cord defined by sectors in the SCS electrode assembly.

There are various other embodiments in which to realize the present invention. The photoemitter may be an IR emitter diode embedded in the electrode array or alternatively, the IR emitter diode may be mounted in the generator device and coupled with the stimulator electrode array via a fiber optic cable.

While the present invention has been described in terms of specific embodiments thereof, it will be understood in view of the present disclosure, that numerous variations upon the invention are now enabled to those skilled in the art, which variations yet reside within the scope of the present teaching. Accordingly, the invention is to be broadly construed and limited only by the scope and spirit of the claims now appended hereto.

The invention claimed is:

1. An apparatus for controlling spinal cord stimulation to a patient comprising:
   a first array of electrodes embedded in a flexible substrate;
   a second array of electrodes embedded in the flexible substrate;
   the first array of electrodes and the second array of electrodes arranged in laterally opposed to positions;
   a set of photoemitters embedded in the flexible substrate;
   a first set of photodetectors embedded in the flexible substrate;
   a second set of photodetectors embedded in the flexible substrate;
   a signal processing unit comprising
   a central processing unit and memory,
   a pulse generator, in communication with the central processing unit, connected to the first and second array of electrodes,
   an optical signal processor, in communication with the central processing unit, connected to the set of photoemitters, the first set of photodetectors and the second set of photo detectors;
   a stimulation controller in communication with the signal processing unit and programmed to control the operation of the signal processing unit;
   wherein the flexible substrate is configured to be implanted in the epidural space adjacent to the spinal cord of the patient and positioned such that light emitted from the first of photoemitters is reflected from the spinal cord of the patient into the first and second set of photodetectors;
   wherein the signal processing unit is further programmed to carry out the steps of:
   measuring a first photodetector value for a photodetector in the first set of photodetectors;
   measuring a second photodetector value for a photodetector in the second set of photodetectors;
   determining a group of electrode settings for at least one electrode in the first array of electrodes and at least one electrode in the second array of electrodes based on the first and second photodetector values;
   adjusting the pulse generator based on the group of electrode settings; and, initiating an electric pulse according to the group of electrode settings to provide spinal cord stimulation.

2. The apparatus of claim 1 wherein the signal processing unit is further programmed to carry out the step of:
computing a ratio of the first photodetector value to the second photodetector value as an optical ratio.

3. The apparatus of claim 1 wherein the signal processing unit is further programmed to carry out the step of:
computing a total of the first photodetector value and the second photodetector value as an optical intensity.

4. The apparatus of claim 1 further comprising a calibration system connected to the signal processing unit and wherein the calibration system is programmed to generate a calibration table comprising the first photodetector value, the second photodetector value and at least one of the group of a set of current pulse amplitudes, a set of current pulse widths, and a set of pulse frequencies.

5. The apparatus of claim 4 wherein the calibration system is further programmed to generate the calibration table in response to a set of patient positions of the patient.

6. The apparatus of claim 5 wherein the calibration system is further programmed to generate the calibration table in response to the set of patient positions corresponding to 0°, 90°, 180° and 270°.

7. The apparatus of claim 1 wherein the step of determining a group of electrode settings includes comparing the first photodetector value and the second photodetector value to a first stored photodetector value and a second stored photodetector value, respectively, in a stored calibration table containing a group of electrode settings.

8. The apparatus of claim 7 wherein the step of determining a group of electrodes settings includes interpolating the group of electrode settings from a calibrated set of electrode settings.

9. The apparatus of claim 8 wherein the step of determining a group of electrode settings includes taking a weighted average of a set of calibrated electrode settings.

10. The apparatus of claim 7 wherein the step of determining a group of electrode settings includes time averaging a set of previous electrode settings.

11. The apparatus of claim 1 further comprising a pulse modulator, connected to the pulse generator and the optical signal processor, for modulating pulses according to an amplitude, a frequency and a pulse width.

12. The apparatus of claim 1 further comprising an optical modulator, connected to the optical signal processor, for modulating light emitted from the first set of photoemitters and the second set of photoemitters.

13. The apparatus of claim 1 the first and second sets of photodetectors and the set of photoemitters comprise a set of emitter/detector devices wherein each emitter/detector device includes at least one photoemitter and at least one photodetector integrated into a single device.

14. The apparatus of claim 13 wherein the first and second sets of photodetectors comprise a set of photodarlington devices.

15. The apparatus of claim 1 wherein the first array of electrodes is positioned in a first column, the second array of electrodes is positioned in a second column; the set of photoemitters is arranged in a third column, the first set of photodetectors is arranged in a fourth column, and the second set of photodetectors is arranged in a fifth column.

16. The apparatus of claim 15 wherein the third column is fixed between the first column and the second column.

17. The apparatus of claim 16 wherein the first column is fixed between the fourth column and the third column, and wherein the second column is fixed between the fifth column and the third column.

18. A method for controlling electrical spinal cord stimulation to a patient comprising: providing a stimulator with a first array of electrodes in a first column, a second array of electrodes in a second column, a set of photoemitters in a third column, a first set of photodetectors in a fourth column, a second set of photodetectors in a fifth column;
implanting the stimulator into the epidural space adjacent the spinal cord;
connecting an electrical pulse generator to the first and second arrays, of electrodes;
connecting an optical signal processor to the first and second sets of photodetectors;
connecting the optical signal processor to the set of photoemitters;
controlling the electrical pulse generator with a central processing unit and the optical signal processor;
directing the set of photoemitters, with the optical signal processor, to send a set of light beams to the spinal cord of the patient;
reflecting the light from at least one light beam in the set of light beams to a first photodetector in the first set of photodetectors;
reflecting the light from the at least one light beam in the set of light beams to a second photodetector in the second set of photodetectors;
measuring a first detected light value from the first photodetector;
measuring a second detected light value from the second photodetector;
determining a group of electrode settings for at least one electrode in the first array of electrodes based on the first detected light value and at least one electrode in the second array of electrodes based on the second detected light value; and,
sending current pulses to the first and second array of electrodes, from the electrical pulse generator, based on the group of electrode settings to effect electrical spinal cord stimulation.

19. The method of claim 18 wherein the step of determining the group of electrode settings includes a step of calibrating the stimulator in response to a set of patient positions.

20. The method of claim 19 wherein the step of calibrating includes the steps of:
generating a calibration table comprising a set of left photodetector values and a set of right photodetector values, and one of the group of a set of current pulse amplitudes, a set of current pulse widths, and a set of pulse frequencies; and,
storing the calibration table in a memory accessible by the central processing unit.

21. The method of claim 20 wherein the step of determining a group of electrode settings includes comparing the first detected light value to the set of left photodetector values and comparing the second detected light value to the set of right photodetector values in the calibration table.

22. The method of claim 21 wherein the step of determining a group of electrode settings includes calculating a weighted average of electrode settings.

23. The method of claim 22 including the steps of:
establishing a communications link between a remote calibration computer and the central processing unit;
performing the step of calibrating using the remote calibration computer; and, downloading the calibration table to the remote calibration computer.

24. The method of claim 21 wherein the step of determining a group of electrodes settings includes further subdividing the first and second arrays of electrodes into sectors.

25. The method of claim 20 wherein the step of determining the group of electrode settings includes interpolating at least one electrode setting of the group of electrode settings from the calibration table using the first detected light value and the second detected light value.

26. The method of claim 25 wherein each of the steps of measuring a first detected light value and measuring a second detected light value include the additional step of demodulating a detected signal from a photodetector in accordance with the step of modulating the set of light beams.

27. The method of claim 18 wherein the step of adjusting current pulses further includes modulating the pulse generator based on at least one step of the group of steps: modulating the pulse amplitude, modulating the pulse width and modulating the pulse frequency.

28. The method of claim 18 wherein the step of directing includes the step of modulating the set of light beams.

29. The method of claim 18 wherein the step of providing the stimulator includes the step of arranging the third column to be situated between the first column and the second column.

30. The method of claim 18 wherein the step of providing the stimulator includes the steps of arranging the first column to be situated between the fourth column and the third column, and arranging the second column to be situated between the third column and the fifth column.

31. The method of claim 18 including the further step of remotely controlling the electrical pulse generator and the optical signal processor.

32. The method of claim 18 including the further step of maintaining constant stimulation intensity to the spinal cord during a set of positional changes.

33. The method of claim 18 including the step of maintaining a constant stimulation electric field strength to a point in the spinal cord during a set of positional changes of the spinal cord.

34. The method of claim 18 including the step of computing a ratio of the first detected light value to the second detected light value as an optical ratio.

35. The method of claim 18 including the step of computing a total light intensity as the sum of the first detected light value and the second detected light value as an optical intensity.

36. The method of claim 18 wherein the step of determining a group of electrode settings includes calculating a time average of previous electrode settings.

37. An apparatus for controlling spinal cord stimulation to a patient comprising:
a first array of electrodes embedded in an elastomer substrate and arranged in a first column;
a second array of electrodes embedded in the elastomer substrate arranged in a second column;
a first set of optical fibers embedded in the elastomer substrate and arranged in a third column;
a second set of optical fibers embedded in the elastomer substrate arranged in a fourth column;
a third set of optical fibers embedded in the elastomer substrate arranged in a fifth column;
a signal processing unit comprising:
a central processing unit and memory;
a pulse generator, in communication with the central processing unit, connected to the first and second arrays of electrodes;
an IR emitter optically, connected to the first set of optical fibers, to insert light into the first set of optical fibers;
a photodetector array, optically connected to the second and third sets of optical fibers;
an optical signal processor, in communication with the central processing unit, connected to the photodetector array;
a stimulation controller, in communication with the signal processing unit and programmed to control the operation of the signal processing unit;
wherein the elastomer substrate is configured to be implanted in the epidural space adjacent to the spinal cord of the patient and positioned such that light emitted by the first set of optical fibers is reflected from the spinal cord of the patient into at least one optical fiber included in the second set of optical fibers and the third set of optical fibers;
wherein the signal processing unit is further programmed to carry out the operations of:
measuring a first photodetector value from the photodetector array;
measuring a second photodetector value from the photodetector array;
determining a group of electrode settings for at least one electrode in the first array of electrodes and at least one electrode in the second array of electrodes based on the first and second photodetector values;
adjusting the pulse generator based on the group of electrode settings; and,
sending a first pulse to at least one electrode in the first array of electrodes and a second pulse to at least one of the second array of electrodes to effect spinal cord stimulation to the patient.

38. The apparatus of claim 37 wherein the first set of optical fibers is terminated at the elastomer substrate in a set of dispersion lenses.

39. The apparatus of claim 37 wherein the second and third sets of optical fibers are terminated at the elastomer substrate in a set of collection lenses.

* * * * *